(12) United States Patent
Toida et al.

(10) Patent No.: US 11,256,170 B2
(45) Date of Patent: *Feb. 22, 2022

(54) COMPOUND, RESIST COMPOSITION, AND METHOD FOR FORMING RESIST PATTERN USING IT

(71) Applicant: Mitsubishi Gas Chemical Company, Inc., Tokyo (JP)

(72) Inventors: Takumi Toida, Kanagawa (JP); Masatoshi Echigo, Tokyo (JP); Takashi Sato, Kanagawa (JP); Youko Shimizu, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,059

(22) PCT Filed: Mar. 2, 2016

(86) PCT No.: PCT/JP2016/056332
§ 371 (c)(1),
(2) Date: Sep. 20, 2017

(87) PCT Pub. No.: WO2016/158168
PCT Pub. Date: Oct. 6, 2016

(65) Prior Publication Data
US 2018/0074406 A1 Mar. 15, 2018

(30) Foreign Application Priority Data
Mar. 31, 2015 (JP) .............................. JP2015-073497

(51) Int. Cl.
| G03F 7/039 | (2006.01) |
| G03F 7/004 | (2006.01) |
| C07D 311/78 | (2006.01) |
| G03F 7/30 | (2006.01) |
| C07D 493/04 | (2006.01) |
| C07C 37/72 | (2006.01) |
| C08G 8/14 | (2006.01) |
| C08G 10/02 | (2006.01) |
| C07D 311/00 | (2006.01) |
| C07D 307/77 | (2006.01) |
| G03F 7/20 | (2006.01) |
| G03F 7/16 | (2006.01) |

(52) U.S. Cl.
CPC .............. *G03F 7/039* (2013.01); *C07C 37/72* (2013.01); *C07D 307/77* (2013.01); *C07D 311/00* (2013.01); *C07D 311/78* (2013.01); *C07D 493/04* (2013.01); *C08G 8/14* (2013.01); *C08G 10/02* (2013.01); *G03F 7/004* (2013.01); *G03F 7/0046* (2013.01); *G03F 7/0392* (2013.01); *G03F 7/20* (2013.01); *G03F 7/16* (2013.01); *G03F 7/30* (2013.01)

(58) Field of Classification Search
CPC ....... G03F 7/0392; G03F 7/30; C07D 307/77; C07D 311/00; C07D 493/04; C07C 37/72; C08G 8/14; C08G 10/02
USPC ................ 430/270.1, 326; 549/382; 568/719
See application file for complete search history.

(56) References Cited

U.S. PATENT DOCUMENTS

| 2,100,798 | A | 11/1937 | Dilthey |
| 2,546,872 | A | 3/1951 | Schmid |
| 2,587,437 | A | 2/1952 | Bralley |
| 3,947,468 | A | 3/1976 | Hall |
| 4,252,884 | A | 2/1981 | Bennett |
| 4,289,839 | A | 9/1981 | Dipippo |
| 4,482,489 | A | 11/1984 | Dipippo |
| 4,579,758 | A | 4/1986 | Dorsch |
| 5,332,648 | A | 7/1994 | Kihara |
| 5,986,094 | A | 11/1999 | Ghoshal et al. |
| 6,784,228 | B2 | 8/2004 | Ogura |
| 6,794,408 | B2 | 9/2004 | Eder |
| 7,871,751 | B2 | 1/2011 | Echigo |
| 9,136,121 | B2 | 9/2015 | Hatakeyama |
| 9,274,426 | B2 | 3/2016 | Rahman |
| 9,316,913 | B2 | 4/2016 | Echigo |
| 9,540,339 | B2 | 1/2017 | Echigo |
| 9,908,831 | B2 | 3/2018 | Echigo |
| 10,303,055 | B2 | 5/2019 | Sato |
| 10,377,734 | B2 | 8/2019 | Echigo |
| 2002/0106909 | A1 | 8/2002 | Kato |
| 2003/0092852 | A1 | 5/2003 | Ogura |
| 2004/0197709 | A1 | 10/2004 | Arase |
| 2005/0074695 | A1 | 4/2005 | Nakamura |
| 2005/0255712 | A1 | 11/2005 | Kato |

(Continued)

FOREIGN PATENT DOCUMENTS

| CN | 1414031 | 4/2003 |
| CN | 1853141 A | 10/2006 |

(Continued)

OTHER PUBLICATIONS

International Search Report on Patentability for PCT/JP2016/056332 dated May 31, 2016; English translation submitted herewith (11 pages).

(Continued)

*Primary Examiner* — John S Chu
(74) *Attorney, Agent, or Firm* — Fitch, Even, Tabin & Flannery LLP

(57) ABSTRACT

The resist composition of the present invention contains one or more selected from compounds represented by specific formulae and resins obtained using these as monomers.

20 Claims, No Drawings

(56) References Cited

U.S. PATENT DOCUMENTS

| | | | |
|---|---|---|---|
| 2007/0059632 A1* | 3/2007 | Oguro | C07D 311/82 430/270.1 |
| 2007/0172759 A1 | 7/2007 | Ogihara | |
| 2007/0232839 A1 | 10/2007 | Yoshitomo | |
| 2007/0275325 A1 | 11/2007 | Hatakeyama | |
| 2008/0113294 A1 | 5/2008 | Echigo et al. | |
| 2008/0138744 A1 | 6/2008 | Hatanaka | |
| 2008/0153031 A1 | 6/2008 | Echigo | |
| 2009/0171061 A1 | 7/2009 | Sue | |
| 2009/0246684 A1 | 10/2009 | Kim | |
| 2009/0261300 A1 | 10/2009 | Watanabe | |
| 2010/0047709 A1* | 2/2010 | Echigo | C07C 37/20 430/270.1 |
| 2010/0099044 A1 | 4/2010 | Hatakeyama | |
| 2010/0104977 A1 | 4/2010 | Hatakeyama | |
| 2010/0136477 A1 | 6/2010 | Ng | |
| 2010/0190107 A1 | 7/2010 | Shibata | |
| 2010/0207516 A1 | 8/2010 | Moriwaki | |
| 2010/0227859 A1 | 9/2010 | Li et al. | |
| 2010/0285407 A1 | 11/2010 | Ogihara | |
| 2010/0316950 A1 | 12/2010 | Oguro | |
| 2011/0177459 A1 | 7/2011 | Ogihara | |
| 2011/0230058 A1 | 9/2011 | Sakamoto et al. | |
| 2011/0274713 A1 | 11/2011 | Burn | |
| 2011/0311920 A1 | 12/2011 | Kinsho | |
| 2012/0064725 A1 | 3/2012 | Kinsho | |
| 2012/0171611 A1 | 7/2012 | Ideno | |
| 2012/0184103 A1 | 7/2012 | Ogihara | |
| 2012/0220112 A1 | 8/2012 | Hatakeyama | |
| 2012/0228584 A1 | 9/2012 | Wigglesworth | |
| 2013/0004896 A1 | 1/2013 | Echigo et al. | |
| 2013/0056653 A1 | 3/2013 | Hatakeyama | |
| 2013/0056654 A1 | 3/2013 | Hatakeyama et al. | |
| 2013/0084705 A1 | 4/2013 | Nakafuji et al. | |
| 2013/0087529 A1 | 4/2013 | Hatakeyama | |
| 2013/0150627 A1 | 6/2013 | Okada | |
| 2014/0186776 A1 | 7/2014 | Uchiyama | |
| 2014/0248556 A1 | 9/2014 | Kato | |
| 2014/0248561 A1* | 9/2014 | Echigo | C07D 311/96 430/281.1 |
| 2014/0308615 A1 | 10/2014 | Echigo et al. | |
| 2014/0319097 A1 | 10/2014 | Kim | |
| 2014/0363768 A1 | 12/2014 | Kinsho et al. | |
| 2014/0363955 A1 | 12/2014 | Hatakeyama et al. | |
| 2014/0363957 A1 | 12/2014 | Hatakeyama | |
| 2014/0363958 A1 | 12/2014 | Hatakeyama | |
| 2015/0030980 A1 | 1/2015 | Echigo et al. | |
| 2015/0037735 A1 | 2/2015 | Yang | |
| 2015/0090691 A1 | 4/2015 | Echigo | |
| 2015/0309403 A1 | 10/2015 | Rahman | |
| 2015/0368224 A1 | 12/2015 | Echigo | |
| 2015/0376157 A1 | 12/2015 | Echigo et al. | |
| 2015/0376158 A1 | 12/2015 | Echigo | |
| 2015/0376202 A1 | 12/2015 | Echigo | |
| 2016/0130243 A1 | 5/2016 | Satou | |
| 2016/0145231 A1 | 5/2016 | Echigo | |
| 2017/0183279 A1 | 6/2017 | Echigo | |
| 2017/0349564 A1* | 12/2017 | Toida | C07D 311/78 |
| 2018/0074402 A1 | 3/2018 | Toida et al. | |
| 2018/0208703 A1 | 7/2018 | Okada et al. | |

FOREIGN PATENT DOCUMENTS

| | | |
|---|---|---|
| CN | 101889247 A | 11/2010 |
| CN | 102070595 | 5/2011 |
| CN | 103304385 A | 9/2013 |
| CN | 103733136 A | 4/2014 |
| CN | 103804196 A | 5/2014 |
| CN | 104557552 A | 4/2015 |
| EP | 1275673 | 1/2003 |
| EP | 1300403 | 4/2003 |
| EP | 1666970 | 6/2006 |
| EP | 2743249 A1 | 6/2014 |
| EP | 2743769 | 6/2014 |
| EP | 2743770 A1 | 6/2014 |
| EP | 3279190 A1 | 2/2018 |
| JP | S48049508 A | 7/1973 |
| JP | 62094841 A | 5/1987 |
| JP | S62191850 A | 8/1987 |
| JP | H01283280 | 11/1989 |
| JP | H04217675 | 8/1992 |
| JP | H05-19463 A | 1/1993 |
| JP | H05034913 A | 2/1993 |
| JP | H05134415 A | 5/1993 |
| JP | H05-163290 A | 6/1993 |
| JP | 05216235 | 8/1993 |
| JP | H06049402 A | 2/1994 |
| JP | H06242607 A | 9/1994 |
| JP | H07215833 | 8/1995 |
| JP | H1025220 | 1/1998 |
| JP | H10-045764 A | 2/1998 |
| JP | H11072925 | 3/1999 |
| JP | 2001042525 | 2/2001 |
| JP | 2002214769 | 7/2002 |
| JP | 2002334869 A | 11/2002 |
| JP | 2002334896 | 11/2002 |
| JP | 2002341542 | 11/2002 |
| JP | 2003-201333 A | 7/2003 |
| JP | 2004177668 A | 6/2004 |
| JP | 2004271838 A | 9/2004 |
| JP | 2005250434 A | 9/2005 |
| JP | 2005266741 A | 9/2005 |
| JP | 2005-326868 A | 11/2005 |
| JP | 2005326838 A | 11/2005 |
| JP | 2005346024 A | 12/2005 |
| JP | 2006036648 | 2/2006 |
| JP | 2006098869 | 4/2006 |
| JP | 2006113136 | 4/2006 |
| JP | 2006160663 | 6/2006 |
| JP | 2006213634 | 8/2006 |
| JP | 2006259482 A | 9/2006 |
| JP | 2007019294 | 1/2007 |
| JP | 2007199653 | 8/2007 |
| JP | 2007226170 A | 9/2007 |
| JP | 2007226204 A | 9/2007 |
| JP | 2007262398 | 10/2007 |
| JP | 2007326847 | 12/2007 |
| JP | 2008065081 | 3/2008 |
| JP | 2008-145539 A | 6/2008 |
| JP | 2008201954 A | 9/2008 |
| JP | 2008239868 | 10/2008 |
| JP | 2009073738 A | 4/2009 |
| JP | 2009098155 A | 5/2009 |
| JP | 2009108313 | 5/2009 |
| JP | 2009155256 | 7/2009 |
| JP | 2009-173623 A | 8/2009 |
| JP | 2009300978 | 12/2009 |
| JP | 2010160189 | 7/2010 |
| JP | 2010170013 | 8/2010 |
| JP | 2010219295 | 9/2010 |
| JP | 2010235643 | 10/2010 |
| JP | 2011068624 | 4/2011 |
| JP | 2011105887 | 6/2011 |
| JP | 2011150023 | 8/2011 |
| JP | 20121687 | 1/2012 |
| JP | 2012-077295 A | 4/2012 |
| JP | 2012068652 | 4/2012 |
| JP | 2012083731 A | 4/2012 |
| JP | 2012145897 | 8/2012 |
| JP | 2013-068928 A | 4/2013 |
| JP | 2013064978 | 4/2013 |
| JP | 2013-083939 A | 5/2013 |
| JP | 2013083833 | 5/2013 |
| JP | 2013087173 | 5/2013 |
| JP | 2013137524 A | 7/2013 |
| JP | 2013253161 | 12/2013 |
| JP | 2014196288 A | 10/2014 |
| JP | 2014205746 | 10/2014 |
| JP | 2015-018220 A | 1/2015 |
| JP | 2015-018221 A | 1/2015 |
| JP | 2015-018223 A | 1/2015 |
| JP | 2015087115 A | 5/2015 |
| JP | 2015514691 A | 5/2015 |

(56) References Cited

FOREIGN PATENT DOCUMENTS

| | | |
|---|---|---|
| JP | 2015-127821 A | 7/2015 |
| KR | 10-2010-0095563 A | 8/2010 |
| WO | 9736960 | 10/1997 |
| WO | 0214434 | 2/2002 |
| WO | 03017002 | 2/2003 |
| WO | 2004066377 A1 | 8/2004 |
| WO | 2005/029189 A1 | 3/2005 |
| WO | 2005111724 | 11/2005 |
| WO | 2006/068267 A1 | 6/2006 |
| WO | 2007097457 | 8/2007 |
| WO | 2008/053974 A1 | 5/2008 |
| WO | 2008/137816 A2 | 11/2008 |
| WO | 2009072465 A1 | 6/2009 |
| WO | 2009119201 A1 | 10/2009 |
| WO | 2009145224 | 12/2009 |
| WO | 2011034062 A1 | 3/2011 |
| WO | 2012165507 A1 | 12/2012 |
| WO | 2013/010102 A2 | 1/2013 |
| WO | 2013/024777 A1 | 2/2013 |
| WO | 2013/024778 A1 | 2/2013 |
| WO | 2013024779 A1 | 2/2013 |
| WO | 2013066067 | 5/2013 |
| WO | 2013184755 | 12/2013 |
| WO | 2014050690 | 4/2014 |
| WO | 2014/123032 A1 | 8/2014 |
| WO | 2014199660 | 12/2014 |

OTHER PUBLICATIONS

Tian-jun Liu, Ke-shen Zhang, Yong-jun Chen, Dong Wang and Chao-jun Li, "Chiral Conjugated Oligomer Based on 1, 1'-Binol With 3, 3 '—Acetylene—Phenylene-Acetylene Spacer", Chinese Journal of Polymer Science, Mar. 8, 2001, vol. 19, No. 5, p. 521-526.
T. Nakayama, M. Nomura, K. Haga, M. Ueda: "A New Three-Component Photoresist Based on Calix[4]resorcinarene Derivative, a Cross-linker, and a Photo-acid Generator" Bull. Chem. Soc. Jpn., 71, 2979 (1998).
International Search Report for PCT/JP2014/051775 dated Feb. 25, 2014 and English translation (4 pages).
Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.
Areephong, Jetsuda, et al., "A concise synthesis of functionalized 7-oxa-[5]-helicenes," Tetrahedron Letters, 2004, vol. 45, pp. 3067-3070.
Bentley, K. W., and Robinson, R., "A Synthesis of alpha-Anhydrotrimethylbrazilone," Tetrahedron Letters, 1959, vol. 1, Issue 2, pp. 11-14.
Brecher, Jonathan, Graphical Representation Standards for Chemical Structure Diagrams, Pure Appl. Chem., 2008, pp. 277-410, vol. 80, No. 2, Cambridge, Massachusetts.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
Cameron, Donald W., et al., "Synthesis of a natural polychloro dinaphthofuran quinone," Tetrahedron Letters, 1980, vol. 21(14), pp. 1385-1386.

Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305.

Clowes, G. A., et al., "Studies of the Scholl reaction: Oxidative Dehydrogenation involving 1-Ethoxynaphthylenen and Related Compounds," J Chem. Soc (C) 2519-2526 (1968).

Dann, von Otto, and Hofmann, Hans, Synthese von ( )-Brasilin, Justus Liebigs Annalen der Chemie, 1963, vol. 667, Issue 1, pp. 116-125.

English Translation of JP H01-283280 A, Nov. 14, 1989.

Ghodratbeigi Mohsen et al., "Design, modeling and synthesis of molecular tweezers with self-assembly Properties," Journal of Molecular Structure, 2011, vol. 990, No. 1, pp. 140-151.

Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.

International Search Report dated Feb. 25, 2014 for PCT/JP2012/051775 and English translation of the same (4 pages).

International Search Report dated Feb. 9, 2016, for PCT/JP2015/084907 and English translation of the same (7 pages).

International Search Report dated Mar. 25, 2014 for International Application No. PCT/JP2014/052524 with English Translation (8 pages).

International Search Report dated May 13, 2014 for International Application No. PCT/JP2014/052530 with English Translation (8 pages).

International Search Report dated Oct. 23, 2012 issued in International Application No. PCT/JP2012/070304.

International Search Report dated Sep. 11, 2012 for International Application No. PCT/JP2012/070305 with English Translation (5 pages).

International Search Report on Patentability for PCT/JP2016/056333 dated May 24, 2016; English translation submitted herewith (7 pages).

Jha Amitabh and Beal Jennifer, "Convenient synthesis of 12H-benzo[a]xanthenes from 2-tetralone," Tetrahedron Letters, 2004, vol. 45, No. 49, pp. 8999-9001.

Journal of the Chemical Society, p. 5336-5341 (Nov. 1963).

Machine English Translation of JP 2008-239868 A, Oct. 9, 2008.

Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.

Nature, 161:930-931 (1948).

Nishiyama Tomihiro et al., Antioxidant activities of fused heterocyclic compounds, xanthene-2,7-diols with BHT or Catechol skeleton, Polymer Degradation and Stability, 1998, vol. 62, No. 3, pp. 529-534.

Ohishi Takeshi. Tetrahedron Letters 42 (2001) 2493-2496.

Shinji Okazaki et al., "New Trends of Photoresists", CMC Publishing Co., Ltd., Sep. 2009, p. 211-259.

Osman A-M, Reactions Between Chloro-p-benzoquinones and Beta-Naphtol, Journal of Organic Chemistry, 1957, vol. 22, pp. 342-344.

Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.

Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.

Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b,fJthiepin, Part CXXXIII in the series Neurotropic and Psychotropic Agents, Collection of Czechoslovak Chemical Communications, 1979, vol. 44, No. 10, pp. 2987-2996.

Protiva, Miroslav, et al., "Potential metabolites or tricyclic neuroleptics 3,7-dimethoxy and 7,8-dimethoxy derivatives of 10-{4-methylpiperazino )-10,11-dihydrodibenzo[b,f]thiepin", Collection of Czechoslovak Chemical Communications, 1981, vol. 46, pp. 1808-1817.

Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.

Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.

(56) References Cited

OTHER PUBLICATIONS

Sirringhaus Henning et al., Dibenzothienobisbenzothiophene—a novel fused-ring oligomer with high field-effect mobility, Journal of Materials Chemistry, 1999, vol. 9, pp. 2095-2101.
Written Opinion of the International Searching Authority issued in International Application No. PCT/JP2012/070304 (including translation), dated Oct. 23, 2012.
European Journal of Medicinal Chemistry, published bi-monthly, Ejmcs, 13(4): 381-385 (1978).
Skandinavisches Archiv fuer Physiologie, 43: 215-243 (1923).
International Preliminary Report on Patentability issued in International Application No. PCT/JP2012/070304.
Hannuksela, Miska M. et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
Luo, Junfei et al., "Salicylic acids as readily available starting materials for the synthesis of meta-substituted biaryls," ChemComm, 2015, vol. 51, pp. 3127-3130.

\* cited by examiner

COMPOUND, RESIST COMPOSITION, AND METHOD FOR FORMING RESIST PATTERN USING IT

TECHNICAL FIELD

The present invention relates to a resist composition and a method for forming a resist pattern using it. Also, the present invention relates to a compound usable in the resist composition and the like. Moreover, the present inventions relates to a method for purifying the compound.

BACKGROUND ART

Conventional typical resist materials are polymer based resist materials capable of forming amorphous thin films. Examples include polymer based resist materials such as polymethyl methacrylate, polyhydroxy styrene with an acid dissociation reactive group, and polyalkyl methacrylate. A line pattern of about 45 to 100 nm is formed by irradiating a resist thin film made by coating a substrate with a solution of such a polymer based resist material with ultraviolet, far ultraviolet, electron beam, extreme ultraviolet (EUV), and X-ray or the like.

However, because polymer based resist materials have a molecular weight as large as about 10,000 to 100,000 and also wide molecular weight distribution, in lithography using a polymer based resist material, roughness occurs on a fine pattern surface; the pattern dimension becomes difficult to be controlled; and the yield decreases. Therefore, there is a limitation in miniaturization with lithography using a conventional polymer based resist material. In order to make a finer pattern, various low molecular weight resist materials have been proposed.

For example, an alkaline development type negative type radiation-sensitive composition (see, for example, Patent Literatures 1 and 2) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 and Non Patent Literature 1) using a low molecular weight cyclic polyphenolic compound as a main component has been suggested as well.

Also, as a base compound of a resist material, a polyphenol compound is known to be capable of imparting high heat resistance despite a low molecular weight and useful for improving the resolution and roughness of a resist pattern (see, for example, Non Patent Literature 2).

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623

Non Patent Literature

Non Patent Literature 1: T. Nakayama, M. Nomura, K. Haga, M. Ueda: Bull. Chem. Soc. Jpn., 71, 2979 (1998)

Non Patent Literature 2: Shinji Okazak et al., "New Trends of Photoresists", CMC Publishing Co., Ltd., September 2009, pp. 211-259

SUMMARY OF INVENTION

Technical Problem

However, the heat resistances of the compositions of Patent Literatures 1 and 2 are not sufficient, and the shapes of the obtained resist patterns are likely to be poor. The solubilities of the compositions of Patent Literature 3 and Non Patent Literature 1 in safe solvents used in a semiconductor production process are not sufficient, also their sensitivities are not sufficient, the shapes of the obtained resist patterns in some cases are poor, and thus a further improvement of low molecular weight resist materials is desired.

Also, Non Patent Literature 2 is silent on solubility, the heat resistances of the described compounds are still not sufficient, and a further improvement of various properties such as heat resistance, water resistance, chemical resistance, electrical properties, and mechanical properties is required.

An object of the present invention is to provide a resist composition which is capable of reducing defects of a film (thin film formation), has good storage stability and high sensitivity, and can impart a good shape to a resist pattern, and a method for forming a resist pattern using the resist composition.

Another object of the present invention is to provide a compound (such as a polyphenol derivative) having high solubility in a safe solvent.

Solution to Problem

The present inventors have, as a result of devoted examinations to solve the above problems, found out that a compound having a specific structure has high solubility in a safe solvent and that a resist composition containing the compound has high sensitivity and can impart a good shape to a resist pattern, and reached the present invention.

More specifically, the present invention is as follows.

[1] A resist composition comprising one or more selected from a compound represented by the following general formula (1), a compound represented by the following general formula (2), and a resin obtained using these as monomers:

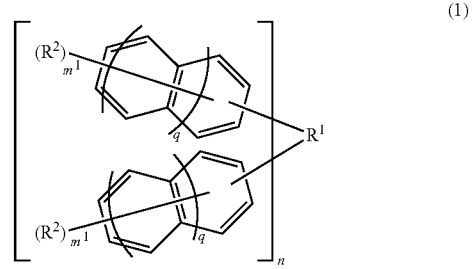

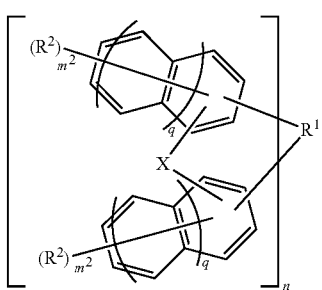

wherein $R^1$ is a single bond or a 2n-valent group of 1 to 30 carbon atoms; each $R^2$ is independently a halogen atom, a linear, branched, or cyclic alkyl group of 1 to 10 carbon atoms, an aryl group of 6 to 10 carbon atoms, an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater in the general formulae (1) and (2), structural formulae of n repeating units may be the same or different; in the general formula (1), each $m^1$ is independently an integer of 0 to 7, provided that at least one $m^1$ is an integer of 1 to 7; in the general formula (2), each X is independently an oxygen atom or a sulfur atom, and each $m^2$ is independently an integer of 0 to 6, provided that at least one $m^2$ is an integer of 1 to 6; and in the general formulae (1) and (2), each q is independently 0 or 1; provided that in the general formulae (1) and (2), at least one $R^2$ is a group obtained by replacing a hydrogen atom of a hydroxy group with an acid dissociation group, and at least one selected from the group consisting of $R^1$ and $R^2$ is a group comprising an iodine atom.

[2] The resist composition according to [1], wherein the compound represented by the above general formula (1) is a compound represented by the following general formula (1-1), and the compound represented by the above general formula (2) is a compound represented by the following general formula (2-1):

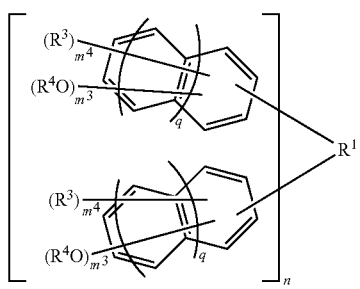

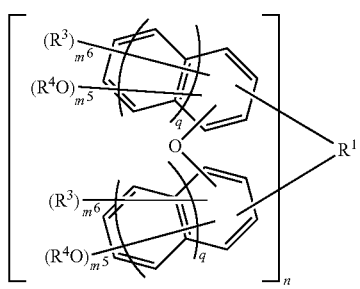

wherein $R^1$ is a single bond or a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater in the general formulae (1-1) and (2-1), structural formulae of n repeating units may be the same or different; in the general formula (1-1), each $m^3$ is independently an integer of 1 to 7, each $m^4$ is independently an integer of 0 to 6, and $m^3+m^4$ is an integer of 1 to 7; in the general formula (2-1), each $m^5$ is independently an integer of 1 to 6, each $m^6$ is independently an integer of 0 to 5, and $m^5+m^6$ is an integer of 1 to 6; and in the general formulae (1-1) and (2-1), each q is independently 0 or 1; provided that in the general formulae (1-1) and (2-1), at least one $R^4$ is an acid dissociation group, and at least one selected from the group consisting of $R^1$ and $R^3$ is a group comprising an iodine atom.

[3] The resist composition according to [1], wherein the compound represented by the above general formula (1) is a compound represented by the following general formula (1-2), and the compound represented by the above general formula (2) is a compound represented by the following general formula (2-2):

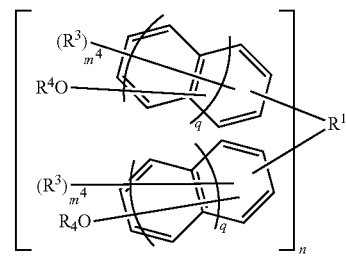

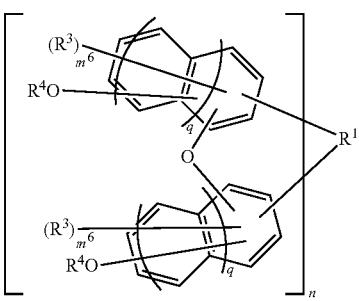

wherein $R^1$ is a single bond or a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater in the general formulae (1-2) and (2-2), structural formulae of n repeating units may be the same or different; in the general formula (1-2), each $m^4$ is independently an integer of 0 to 6; in the general formula (2-2), each $m^6$ is independently an integer of 0 to 5; and in the general formulae (1-2) and (2-2), each q is independently 0 or 1;

provided that in the general formulae (1-2) and (2-2), at least one R⁴ is an acid dissociation group, and at least one selected from the group consisting of R¹ and R³ is a group comprising an iodine atom.

[4] The resist composition according to any of [1] to [3], further comprising a solvent.

[5] The resist composition according to any of [1] to [4], further comprising an acid generating agent.

[6] The resist composition according to any of [1] to [5], further comprising an acid diffusion controlling agent.

[7] A method for forming a resist pattern, comprising the steps of coating a substrate with the resist composition according to any of [1] to [6], thereby forming a resist film; exposing the formed resist film; and developing the exposed resist film.

[8] The resist composition according to any of [1] and [4] to [6], wherein the compound represented by the above general formula (1) is a compound represented by the following general formula (3), and the compound represented by the above general formula (2) is a compound represented by the following general formula (4):

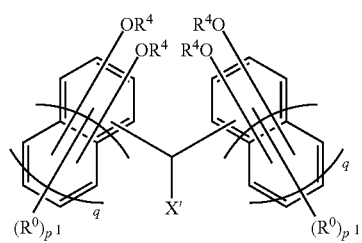

(3)

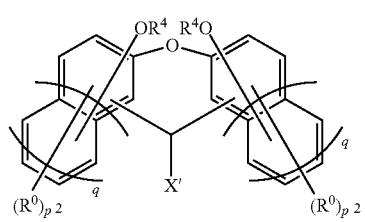

(4)

wherein X' is a hydrogen atom, a halogen atom, or a monovalent group of 1 to 18 carbon atoms; each R⁰ is independently an alkyl group of 1 to 4 carbon atoms or a halogen atom, and may be the same or different on the same naphthalene ring or benzene ring; R⁴ is a hydrogen atom or an acid dissociation group; in the general formula (3), each p¹ is independently an integer of 0 to 5; in the general formula (4), each p² is independently an integer of 0 to 5; and in the general formulae (3) and (4), each q is independently 0 or 1; provided that in the general formulae (3) and (4), at least one R⁴ is an acid dissociation group, and at least one selected from the group consisting of X' and R⁰ is a group comprising an iodine atom.

[9] A compound represented by the following general formula (1):

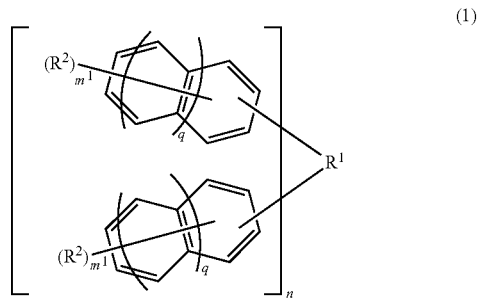

(1)

wherein R¹ is a single bond or a 2n-valent group of 1 to 30 carbon atoms; each R² is independently a halogen atom, a linear, branched, or cyclic alkyl group of 1 to 10 carbon atoms, an aryl group of 6 to 10 carbon atoms, or an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater, structural formulae of n repeating units may be the same or different; each m¹ is independently an integer of 0 to 7, provided that at least one m¹ is an integer of 1 to 7; and each q is independently 0 or 1; provided that in the general formula (1), at least one R² is a group obtained by replacing a hydrogen atom of a hydroxy group with an acid dissociation group, and at least one selected from the group consisting of R¹ and R² is a group comprising an iodine atom.

[10] The compound according to [9], wherein the compound represented by the above general formula (1) is a compound represented by the following general formula (1-1):

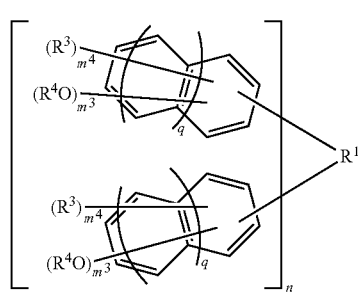

(1-1)

wherein R¹ is a single bond or a 2n-valent group of 1 to 30 carbon atoms; each R³ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each R⁴ is independently a hydrogen atom or an acid dissociation group; n is an integer of 1 to 4, and when n is an integer of 2 or greater, structural formulae of n repeating units may be the same or different; each m³ is independently an integer of 1 to 7, each m⁴ is independently an integer of 0 to 6, and m³+m⁴ is an integer of 1 to 7; and each q is independently 0 or 1; provided that in the general formula (1-1), at least one R⁴ is an acid dissociation group, and at least one selected from the group consisting of R¹ and R³ is a group comprising an iodine atom.

[11] The compound according to [9], wherein the compound represented by the above general formula (1) is a compound represented by the following general formula (1-2):

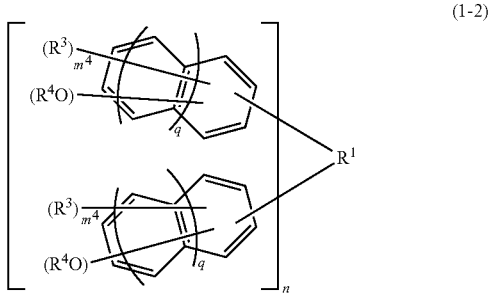

wherein $R^1$ is a single bond or a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^4$ is independently an integer of 0 to 6, and each q is independently 0 or 1; provided that in the general formula (1-2), at least one $R^4$ is an acid dissociation group, and at least one selected from the group consisting of $R^1$ and $R^3$ is a group comprising an iodine atom.

[12] The compound according to [9], wherein the compound represented by the above general formula (1) is a compound represented by the following general formula (3):

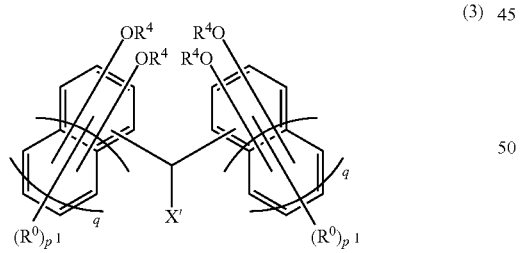

wherein X' is a hydrogen atom, a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; each $p^1$ is independently an integer of 0 to 5; and each q is independently 0 or 1; provided that in the general formula (3), at least one $R^4$ is an acid dissociation group, and at least one selected from the group consisting of X' and $R^0$ is a group comprising an iodine atom.

[13] A compound represented by the following general formula (2):

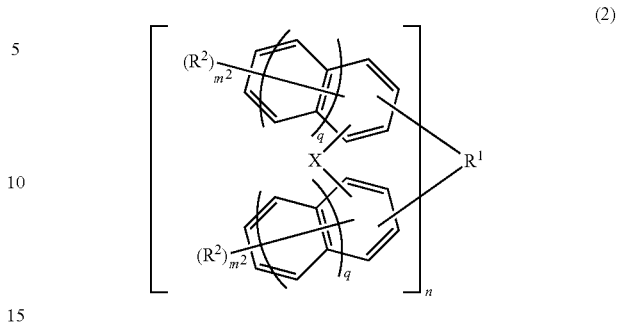

wherein $R^1$ is a single bond or a 2n-valent group of 1 to 30 carbon atoms; each $R^2$ is independently a halogen atom, a linear, branched, or cyclic alkyl group of 1 to 10 carbon atoms, an aryl group of 6 to 10 carbon atoms, or an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater, structural formulae of n repeating units may be the same or different; each X is independently an oxygen atom or a sulfur atom; each $m^2$ is independently an integer of 0 to 6, provided that at least one $m^2$ is an integer of 1 to 6; and each q is independently 0 or 1; provided that in the general formula (2), at least one $R^2$ is a group obtained by replacing a hydrogen atom of a hydroxy group with an acid dissociation group, and at least one selected from the group consisting of $R^1$ and $R^2$ is a group comprising an iodine atom.

[14] The compound according to [13], wherein the compound represented by the above general formula (2) is a compound represented by the following general formula (2-1):

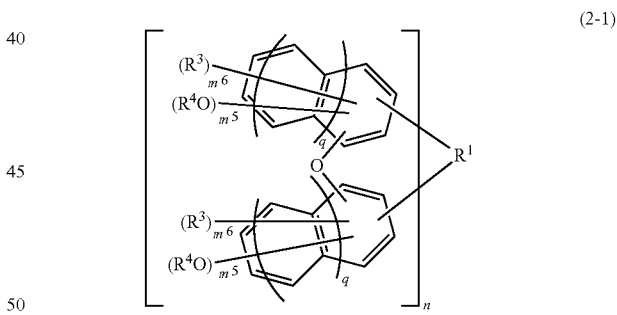

wherein $R^1$ is a single bond or a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^5$ is independently an integer of 1 to 6, each $m^6$ is independently an integer of 0 to 5, and $m^5+m^6$ is an integer of 1 to 6; and each q is independently 0 or 1; provided that in the general formula (2-1), at least one $R^4$ is an acid dissociation group, and at least one selected from the group consisting of $R^1$ and $R^3$ is a group comprising an iodine atom.

[15] The compound according to [13], wherein the compound represented by the above general formula (2) is a compound represented by the following general formula (2-2):

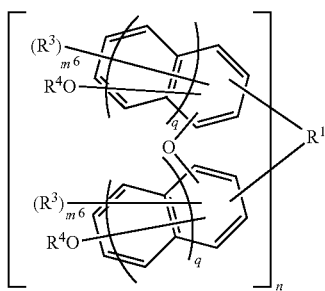

(2-2)

wherein $R^1$ is a single bond or a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^6$ is independently an integer of 0 to 5, and each q is independently 0 or 1; provided that in the general formula (2-2), at least one $R^4$ is an acid dissociation group, and at least one selected from the group consisting of $R^1$ and $R^3$ is a group comprising an iodine atom.

[16] The compound according to [13], wherein the compound represented by the above general formula (2) is a compound represented by the following general formula (4):

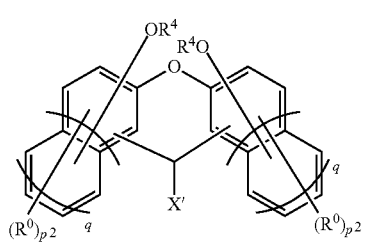

(4)

wherein X' is a hydrogen atom, a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; each $p^2$ is independently an integer of 0 to 5; and each q is independently 0 or 1; provided that in the general formula (4), at least one $R^4$ is an acid dissociation group, and at least one selected from the group consisting of X' and $R^0$ is a group comprising an iodine atom.

[17] A resin obtained by using the compound according to any of [9] to [16] as a monomer.

[18] The resin according to [17] obtained by reacting the compound according to any of [9] to [16] with a crosslinking compound.

[19] The resin according to [18], wherein the crosslinking compound is an aldehyde, a ketone, a carboxylic acid, a carboxylic acid halide, a halogen-containing compound, an amino compound, an imino compound, an isocyanate, or an unsaturated hydrocarbon group-containing compound.

[20] A purification method comprising the steps of:
obtaining a solution (A) by dissolving the compound according to any of [9] to [16] or the resin according to any of [17] to [19] in a solvent; and
extracting impurities in the compound by bringing the obtained solution (A) into contact with an acidic aqueous solution (a first extraction step), wherein
the solvent used in the step of obtaining the solution (A) comprises an organic solvent that does not inadvertently mix with water.

[21] The purification method according to [20], wherein
the acidic aqueous solution is an aqueous mineral acid solution or an aqueous organic acid solution;
the aqueous mineral acid solution is one or more aqueous mineral acid solutions selected from the group consisting of hydrochloric acid, sulfuric acid, nitric acid, and phosphoric acid; and
the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

[22] The purification method according to [20] or [21], wherein the organic solvent that does not inadvertently mix with water is one or more organic solvents selected from the group consisting of toluene, 2-heptanone, cyclohexanone, cyclopentanone, methyl isobutyl ketone, propylene glycol monomethyl ether acetate, and ethyl acetate.

[23] The purification method according to any of [20] to [22], comprising the step of extracting impurities in the compound by further bringing a solution phase comprising the compound into contact with water after the first extraction step (a second extraction step).

Advantageous Effects of Invention

According to the present invention, it is possible to provide a compound having high solubility in a safe solvent and possible to provide a resist composition which contains the compound, is capable of reducing defects of a film (thin film formation), has good storage stability and high sensitivity, and can impart a good shape to a resist pattern, and a method for forming a resist pattern using it.

Moreover, according to the present invention, it is possible to provide a compound (such as a polyphenol derivative) having high solubility in a safe solvent.

DESCRIPTION OF EMBODIMENTS

Hereinafter, an embodiment of the present invention will be described (hereinafter, referred to as "present embodiment"). The present embodiment is given in order to illustrate the present invention. The present invention is not limited to only the present embodiment.

[Resist Composition]

The resist composition of the present embodiment contains one or more selected from a compound represented by the above general formula (1), a compound represented by the above general formula (2), and a resin obtained using any of these compounds as a monomer.

(Resist Composition of First Embodiment)

The first embodiment of the resist composition of the present embodiment contains a compound represented by the following general formula (1).

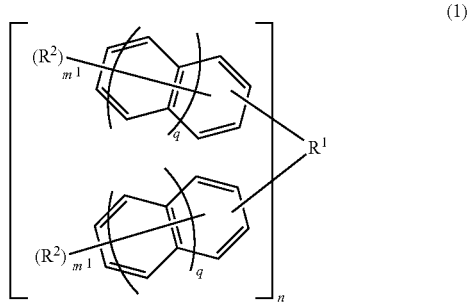

(1)

In the general formula (1), $R^1$ is a single bond or a 2n-valent group of 1 to 30 carbon atoms; herein, the 2n-valent group of 1 to 30 carbon atoms may have an alicyclic hydrocarbon group, a double bond, a hetero atom, or an aromatic group of 6 to 30 carbon atoms; in the general formula (1), each $R^2$ is independently a halogen atom, a linear, branched, or cyclic alkyl group of 1 to 10 carbon atoms, an aryl group of 6 to 10 carbon atoms, or an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater in the general formula (1), structural formulae of n repeating units may be the same or different; in the general formula (1), each $m^1$ is independently an integer of 0 to 7, provided that at least one $m^1$ is an integer of 1 to 7; and in the general formula (1), each q is independently 0 or 1; provided that in the general formula (1), at least one $R^2$ is a group obtained by replacing a hydrogen atom of a hydroxy group with an acid dissociation group, and at least one selected from the group consisting of $R^1$ and $R^2$ is a group containing an iodine atom.

The "at least one selected from the group consisting of $R^1$ and $R^2$" means "at least one group selected from the group consisting of $R^1$ and $R^2$", and does not mean "at least one kind of group selected from the group consisting of $R^1$ and $R^2$".

The chemical structure of the above compound to be contained in the resist composition of the present embodiment can be determined by $^1$H-NMR analysis.

The above compound to be contained in the resist composition of the present embodiment has excellent heat resistance because the compound has a benzene skeleton or a naphthalene skeleton as shown in the above general formula (1).

In the above general formula (1), n is an integer of 1 to 4, and when n is an integer of 2 or greater, the structural formulae of n repeating units may be the same or different. In terms of resist characteristics such as heat resistance, resolution, and roughness, n is preferably 1 to 3 in the above general formula (1). Also, in the above general formula (1), q is preferably 1. That is to say, the compound represented by the above general formula (1) is preferably a compound represented by the following general formula (1-a).

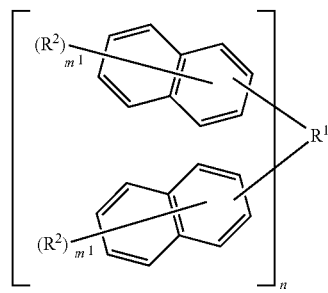

(1-a)

In the general formula (1-a), $R^1$, $R^2$, n, and $m^1$ are as defined in the above general formula (1).

In the present embodiment, although the compound represented by the above general formula (1) is not a polymer, the structure of the [ ] portion bonded to $R^1$ in the above general formula (1) is referred to as the structural formula of the repeating unit (hereinafter, the same also applies to the general formula (2)).

In the above general formula (1), $R^1$ is a single bond or a 2n-valent group of 1 to 30 carbon atoms (hereinafter sometimes referred to as "C1-30"), and the group may have an alicyclic hydrocarbon group, a double bond, a heteroatom, or a C6-30 aromatic group.

The above 2n-valent group refers to a C1-30 alkylene group (n=1), a C1-30 alkanetetrayl group (n=2), a C2-30 alkanehexayl group (n=3), or a C3-30 alkaneoctayl group (n=4). Examples of the 2n-valent group include those having a linear, branched, or cyclic structure.

Also, the 2n-valent group may have an alicyclic hydrocarbon group, a double bond, a hetero atom, or a C6-30 aromatic group. Herein, the alicyclic hydrocarbon group also includes bridged alicyclic hydrocarbon groups.

In the above general formula (1), $R^1$ preferably has a condensed polycyclic aromatic group (in particular, a condensed ring structure of 2 to 4 rings) in terms of heat resistance, and preferably has a polyphenyl group such as a biphenyl group in terms of solubility in a safe solvent and heat resistance.

In the above general formula (1), each $R^2$ is independently a halogen atom, a C1-10 linear, branched, or cyclic alkyl group, a C6-10 aryl group, a C2-10 alkenyl group, a hydroxy group, or a group obtained by replacing a hydrogen atom of a hydroxy group with an acid dissociation group, and may be the same or different on the same naphthalene ring or benzene ring, at least one $R^2$ is a group obtained by replacing a hydrogen atom of a hydroxy group with an acid dissociation group, and each $m^1$ is independently an integer of 0 to 7, provided that at least one $m^1$ is an integer of 1 to 7.

In terms of suppression of device contamination during resist film exposure, $R^2$ is preferably a hydrogen atom, a C1-10 linear, branched, or cyclic alkyl group, a C6-10 aryl group, a C2-10 alkenyl group, or a hydroxy group.

In the above general formula (1), at least one selected from the group consisting of $R^1$ and $R^2$ is a group containing an iodine atom.

Due to the above structural features, the compound represented by the above formula (1) has high heat resistance attributable to its rigidity in spite of its low molecular weight, and is usable even under high temperature baking conditions. Since the resist composition of the present embodiment contains such a compound that has a low molecular weight and can be baked at a high temperature, the resist composition is highly sensitive and, further, can impart a good shape to a resist pattern.

In the present embodiment, in terms of solubility in a safe solvent and resist pattern characteristics, the compound represented by the above formula (1) is preferably a compound represented by the following general formula (1-1).

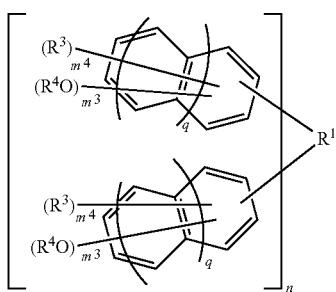

(1-1)

In the general formula (1-1), $R^1$ is as defined in the above general formula (1). In the general formula (1-1), each $R^3$ is independently a halogen atom, a C1-10 linear, branched, or cyclic alkyl group, a C6-10 aryl group, or a C2-10 alkenyl group, provided that in the general formula (1-1), at least one selected from the group consisting of $R^1$ and $R^3$ is a group containing an iodine atom.

The "at least one selected from the group consisting of $R^1$ and $R^3$" means "at least one group selected from the group consisting of $R^1$ and $R^3$", and does not mean "at least one kind of group selected from the group consisting of $R^1$ and $R^3$".

In the general formula (1-1), each $m^3$ is independently an integer of 1 to 7, each $m^4$ is independently an integer of 0 to 6, and $m^3+m^4$ is an integer of 1 to 7. In the general formula (1-1), n is an integer of 1 to 4. In the general formula (1-1), each q is independently 0 or 1, and q is preferably 1. That is to say, the compound represented by the general formula (1-1) is preferably a compound represented by the following general formula (1-1-a).

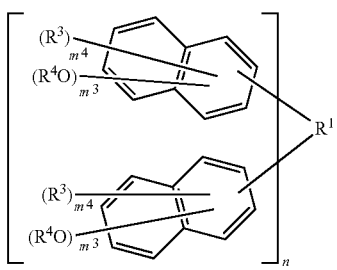

(1-1-a)

In the general formula (1-1-a), each $R^4$ is independently an acid dissociation group or a hydrogen atom, and at least one is an acid dissociation group. In the present specification, the "acid dissociation group" refers to a characteristic group that is cleaved in the presence of an acid and thereby converted into an alkali soluble group or the like. Examples of the "alkali soluble group" include, but not particularly limited to, a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The acid dissociation group is not particularly limited, and can be arbitrarily selected for use from among those proposed in hydroxystyrene based resins, (meth)acrylic acid based resins, and the like used in chemical amplification resist compositions for KrF or ArF. Specific examples include, but not particularly limited to, a substituted methyl group, a 1-substituted ethyl group, a 1-substituted n-propyl group, a 1-branched alkyl group, a silyl group, an acyl group, a 1-substituted alkoxymethyl group, a cyclic ether group, an alkoxycarbonyl group, and an alkoxycarbonylalkyl group. The acid dissociation group preferably has no crosslinkable functional group.

Examples of the substituted methyl group include, but not particularly limited to, substituted methyl groups of 2 to 20 carbon atoms, preferable are substituted methyl groups of 4 to 18 carbon atoms, and more preferable are substituted methyl groups of 6 to 16 carbon atoms. Specific examples can include, but not particularly limited to, a methoxymethyl group, a methylthiomethyl group, an ethoxymethyl group, a n-propoxymethyl group, an isopropoxymethyl group, a n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and a substituent represented by the following formulae (13-1). $R^2$ in the following formulae (13-1) is not particularly limited, and examples include a methyl group, an ethyl group, an isopropyl group, a n-propyl group, a t-butyl group, and a n-butyl group.

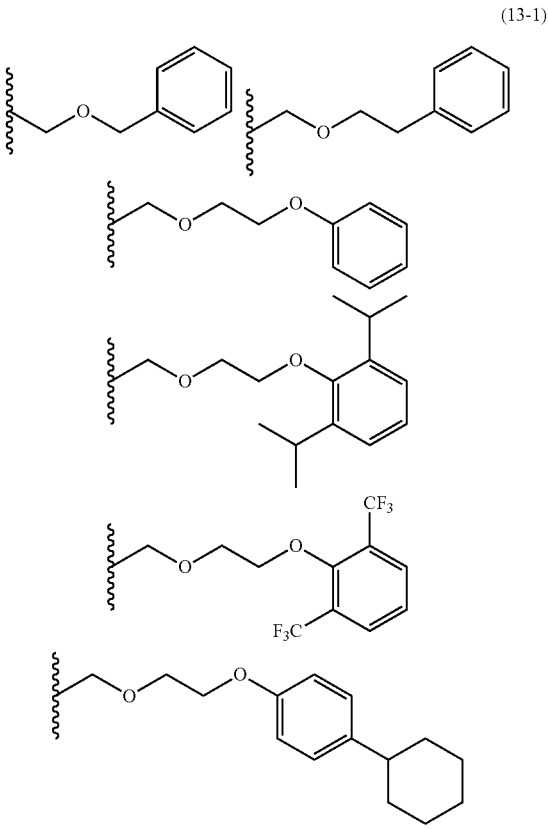

(13-1)

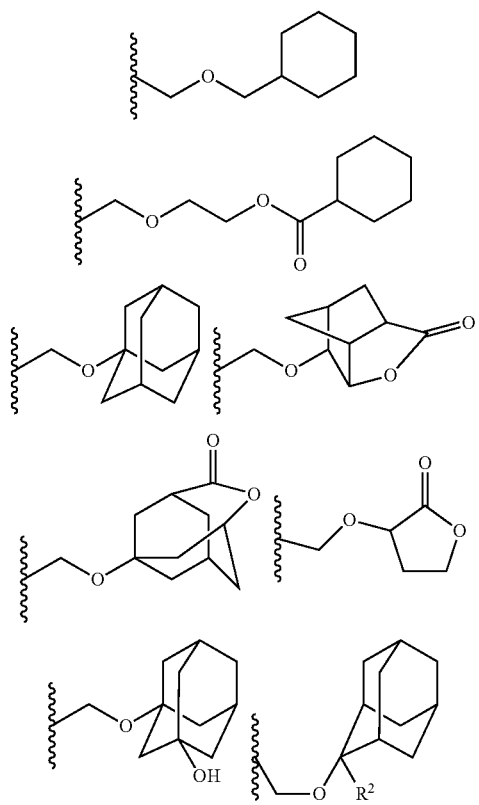

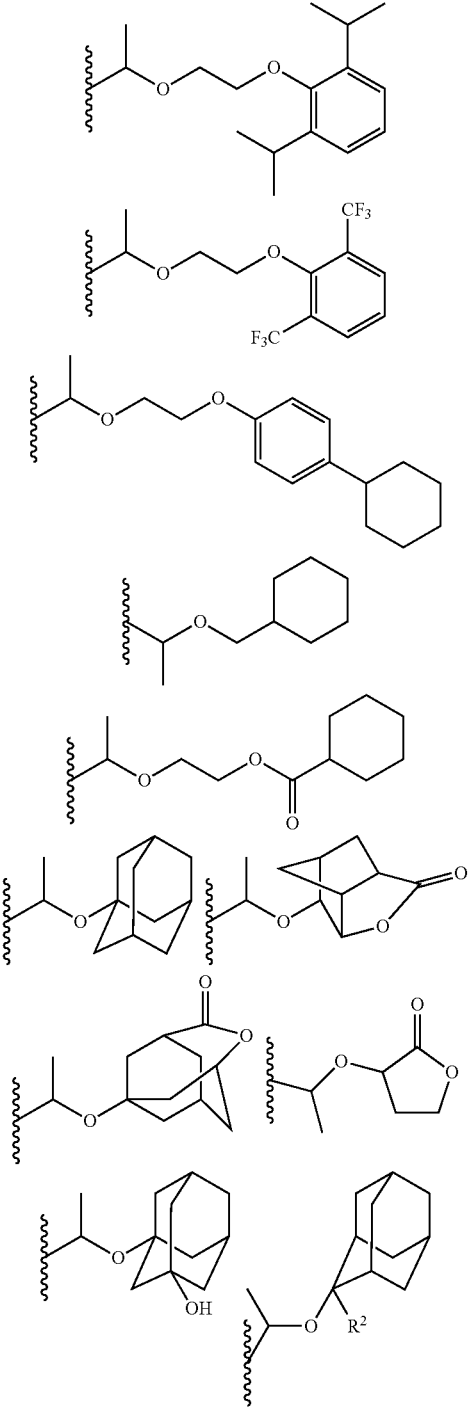

In the formulae (13-1), $R^2$ is an alkyl group of 1 to 4 carbon atoms.

Examples of the 1-substituted ethyl group include, but not particularly limited to, 1-substituted ethyl groups of 3 to 20 carbon atoms, preferable are 1-substituted ethyl groups of 5 to 18 carbon atoms, and more preferable are 1-substituted ethyl groups of 7 to 16 carbon atoms. Specific examples include, but not particularly limited to, a 1-methoxyethyl group, a 1-methylthioethyl group, a 1,1-dimethoxyethyl group, a 1-ethoxyethyl group, a 1-ethylthioethyl group, a 1,1-diethoxyethyl group, a n-propoxyethyl group, an iso-propoxyethyl group, a n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and a substituent represented by the following formulae (13-2).

(13-2)

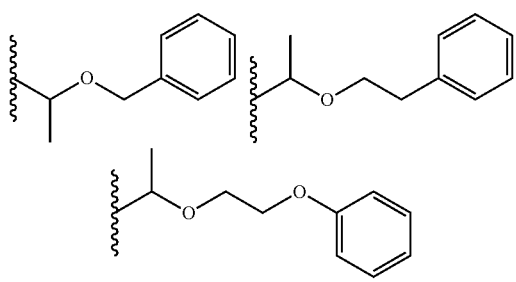

In the formulae (13-2), $R^2$ is as defined in the above formula (13-1).

Examples of the 1-substituted n-propyl group include, but not particularly limited to, 1-substituted n-propyl groups of 4 to 20 carbon atoms, preferable are 1-substituted n-propyl group of 6 to 18 carbon atoms, and more preferable are 1-substituted n-propyl groups of 8 to 16 carbon atoms. Specific examples include, but not particularly limited to, a 1-methoxy-n-propyl group and a 1-ethoxy-n-propyl group.

Examples of the 1-branched alkyl group include, but not particularly limited to, 1-branched alkyl groups of 3 to 20 carbon atoms, preferable are 1-branched alkyl groups of 5 to 18 carbon atoms, and more preferable are branched alkyl groups of 7 to 16 carbon atoms. Specific examples can include, but are not limited to, an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

Examples of the silyl group include, but not particularly limited to, silyl groups of 1 to 20 carbon atoms, preferable are silyl groups of 3 to 18 carbon atoms, and more preferable are silyl groups of 5 to 16 carbon atoms. Specific examples can include, but not particularly limited to, a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, and a triphenylsilyl group.

Examples of the acyl group include, but not particularly limited to, acyl groups of 2 to 20 carbon atoms, preferable are acyl groups of 4 to 18 carbon atoms, and more preferable are acyl groups of 6 to 16 carbon atoms. Specific examples can include, but not particularly limited to, an acetyl group, a phenoxyacetyl group, a propionyl group, a butyryl group, a heptanoyl group, a hexanoyl group, a valeryl group, a pivaloyl group, an isovaleryl group, a lauroyl group, an adamantylcarbonyl group, a benzoyl group, and a naphthoyl group.

Examples of the 1-substituted alkoxymethyl group include, but not particularly limited to, 1-substituted alkoxymethyl groups of 2 to 20 carbon atoms, preferable are 1-substituted alkoxymethyl groups of 4 to 18 carbon atoms, and more preferable are 1-substituted alkoxymethyl groups of 6 to 16 carbon atoms. Specific examples can include, but not particularly limited to, a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

Examples of the cyclic ether group include, but not particularly limited to, cyclic ether groups of 2 to 20 carbon atoms, preferable are cyclic ether groups of 4 to 18 carbon atoms, and more preferable are cyclic ether groups of 6 to 16 carbon atoms. Specific examples can include, but not particularly limited to, a tetrahydropyranyl group, a tetrahydrofuranyl group, a tetrahydrothiopyranyl group, a tetrahydrothiofuranyl group, a 4-methoxytetrahydropyranyl group, and a 4-methoxytetrahydrothiopyranyl group.

Examples of the alkoxycarbonyl group include, but not particularly limited to, alkoxycarbonyl groups of 2 to 20 carbon atoms, preferable are alkoxycarbonyl groups of 4 to 18 carbon atoms, and more preferable are alkoxycarbonyl groups of 6 to 16 carbon atoms. Specific examples can include, but not particularly limited to, a methoxycarbonyl group, an ethoxycarbonyl group, a n-propoxycarbonyl group, an isopropoxycarbonyl group, a n-butoxycarbonyl group, a tert-butoxycarbonyl group, and an acid dissociation group represented by the following formulae (13-3) wherein n=0.

Examples of the alkoxycarbonylalkyl group include, but not particularly limited to, alkoxycarbonylalkyl groups of 2 to 20 carbon atoms, preferable are alkoxycarbonylalkyl groups of 4 to 18 carbon atoms, and more preferable are alkoxycarbonylalkyl groups of 6 to 16 carbon atoms. Specific examples can include, but not particularly limited to, a methoxycarbonylmethyl group, an ethoxycarbonylmethyl group, a n-propoxycarbonylmethyl group, an isopropoxycarbonylmethyl group, a n-butoxycarbonylmethyl group, and an acid dissociation group represented by the following formulae (13-3) wherein n=1 to 4.

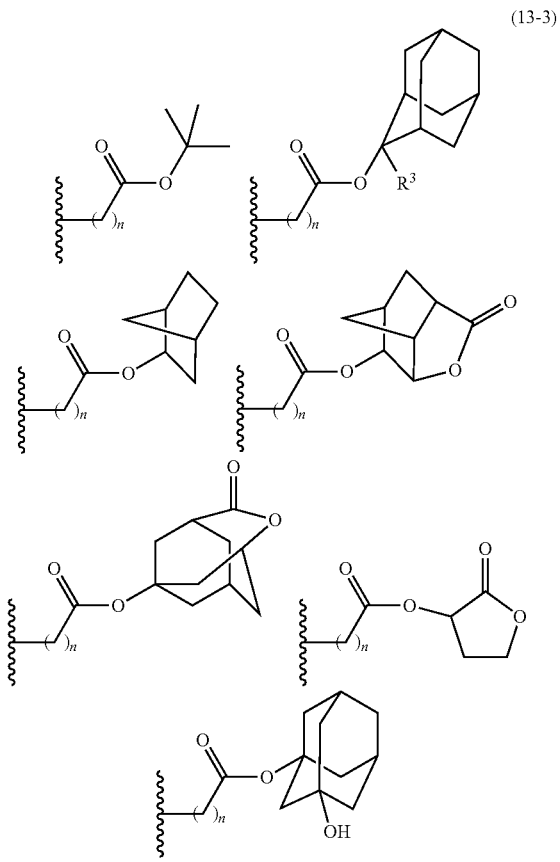

(13-3)

In the formulae (13-3), $R^3$ is a hydrogen atom or a linear or branched alkyl group of 1 to 4 carbon atoms, and n is an integer of 0 to 4.

Among these acid dissociation groups, a substituted methyl group, a 1-substituted ethyl group, a 1-substituted alkoxymethyl group, a cyclic ether group, an alkoxycarbonyl group, and an alkoxycarbonylalkyl group are preferable. A substituted methyl group, a 1-substituted ethyl group, an alkoxycarbonyl group, and an alkoxycarbonylalkyl group are more preferable because of high sensitivity. An acid dissociation group having a structure selected from cycloalkanes of 3 to 12 carbon atoms, lactones, and aromatic rings of 6 to 12 carbon atoms are still more preferable. The cycloalkane of 3 to 12 carbon atoms may be monocyclic or polycyclic and is more preferably polycyclic. Specific examples include, but not particularly limited to, monocycloalkanes, bicycloalkanes, tricycloalkanes, and tetracycloalkanes, and more specific examples include, but not particularly limited to, monocycloalkanes such as cyclopropane, cyclobutane, cyclopentane, and cyclohexane, and polycycloalkanes such as adamantane, norbornane, isobornane, tricyclodecane, and tetracyclodecane. Among these, adamantane, tricyclodecane, and tetracyclodecane are preferable, and adamantane and tricyclodecane are particularly preferable. The cycloalkane of 3 to 12 carbon atoms may have a substituent. Examples of the lactone include, but not particularly limited to, butyrolactone and cycloalkane groups of 3 to 12 carbon atoms having a lactone group. Examples of the aromatic ring of 6 to 12 carbon atoms include, but not particularly limited to, a benzene ring, a naphthalene ring, an anthracene ring, a phenanthrene ring, and a pyrene ring. A benzene ring and a naphthalene ring are preferable, and a naphthalene ring is particularly preferable.

An acid dissociation group selected from the group consisting of the groups represented by the following formulae (13-4) is preferable because of high resolution.

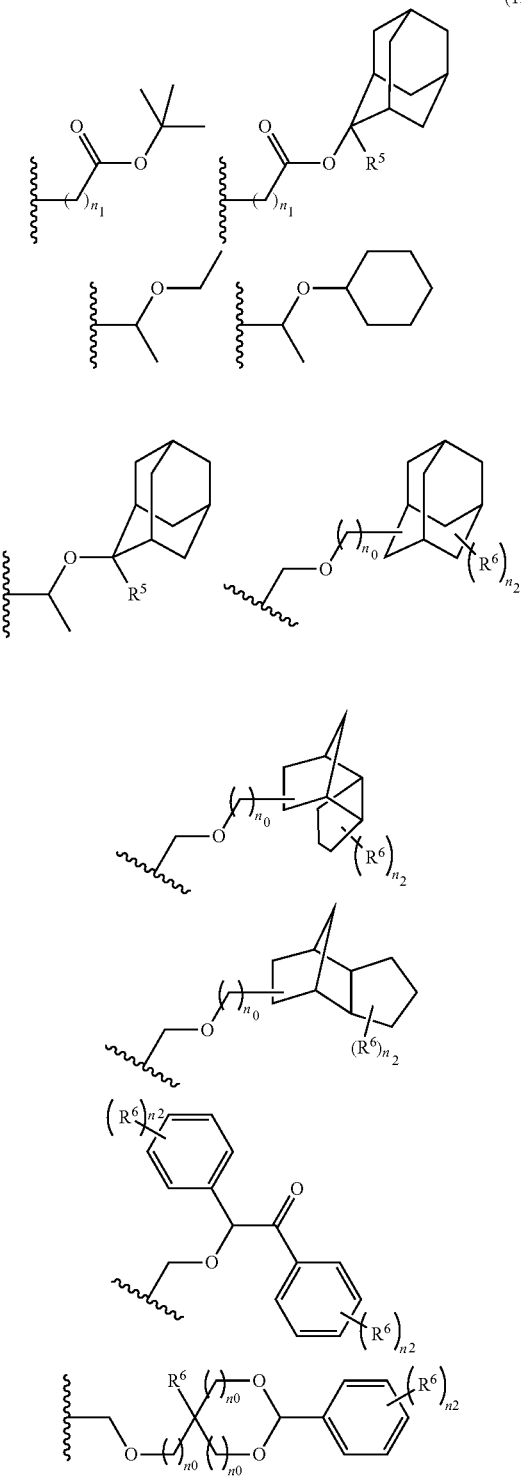

(13-4)

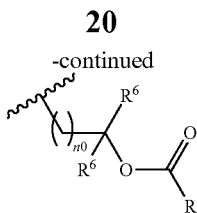

In the formulae (13-4), $R^5$ is a hydrogen atom or a linear or branched alkyl group of 1 to 4 carbon atoms; $R^6$ is hydrogen, a linear or branched alkyl group of 1 to 4 carbon atoms, a cyano group, a nitro group, a heterocyclic group, a halogen atom, or a carboxyl group; $n_1$ is an integer of 0 to 4; $n_2$ is an integer of 1 to 5; and $n_0$ is an integer of 0 to 4.

In terms of sensitivity when formed into a resist composition in the present embodiment, the compound represented by the above general formula (1) is preferably a compound represented by the following general formula (1-2).

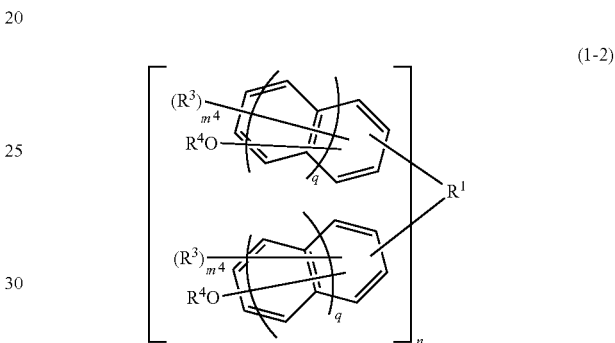

(1-2)

In the above general formula (1-2), $R^1$, $R^3$, $R^4$, $m^4$, n, and q are as defined in the above general formula (1-1), and at least one selected from the group consisting of $R^1$ and $R^3$ is a group containing an iodine atom.

In the above general formula (1-2), q is more preferably 1. That is to say, the compound represented by the above general formula (1) is more preferably a compound represented by the following general formula (1-2-a).

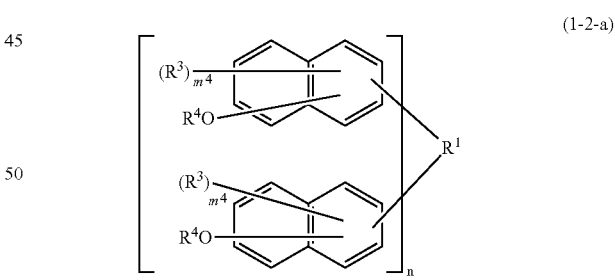

(1-2-a)

In the above general formula (1-2-a), $R^1$, $R^3$, $R^4$, $m^4$, and n are as defined in the above general formula (1-1), and at least one selected from the group consisting of $R^1$ and $R^3$ is a group containing an iodine atom.

In terms of solubility, and sensitivity when formed into a resist composition, $m^3$ is preferably 2 in the above general formula (1-1).

In terms of resist characteristics such as heat resistance, sensitivity, resolution, and roughness in the present embodiment, the compound represented by the above general formula (1-1) is preferably a compound of the above general formula (1-1) wherein n is 1.

In terms of solubility in the present embodiment, the compound represented by the above general formula (1-1) is more preferably a compound represented by the following general formula (1-3).

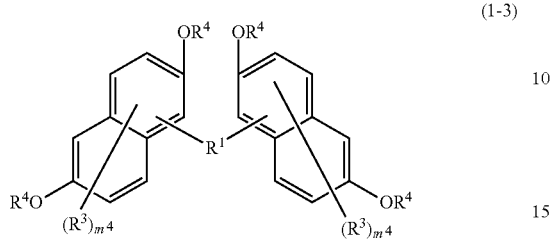

(1-3)

In the general formula (1-3), $R^1$, $R^3$, $R^4$, and $m^4$ are as defined in the above general formula (1-1), and at least one selected from the group consisting of $R^1$ and $R^3$ is a group containing an iodine atom.

Specific examples of the compound represented by the above general formula (1) can include, but not limited to, the followings.

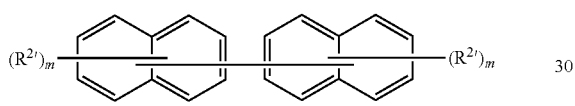

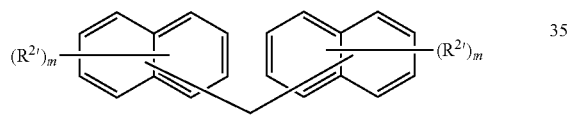

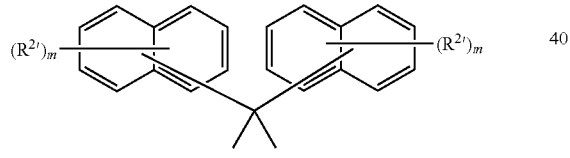

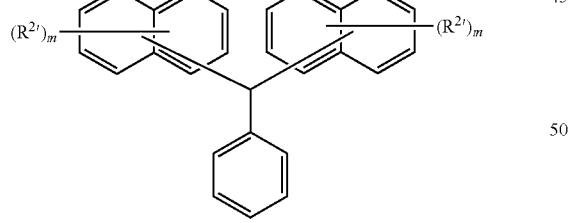

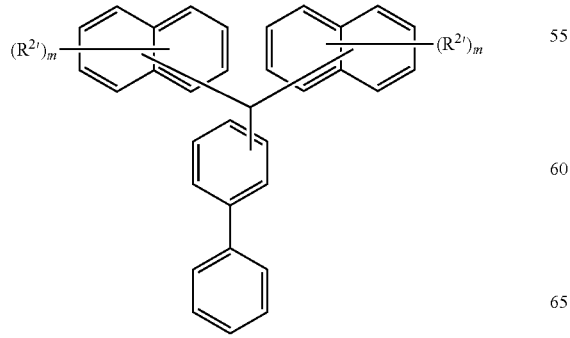

-continued

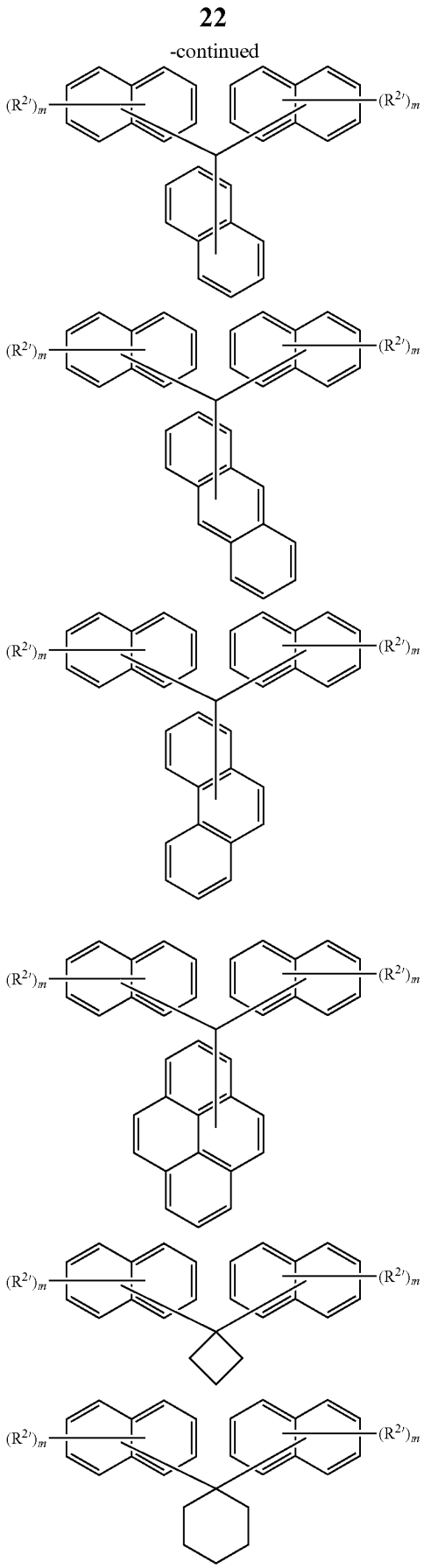

-continued
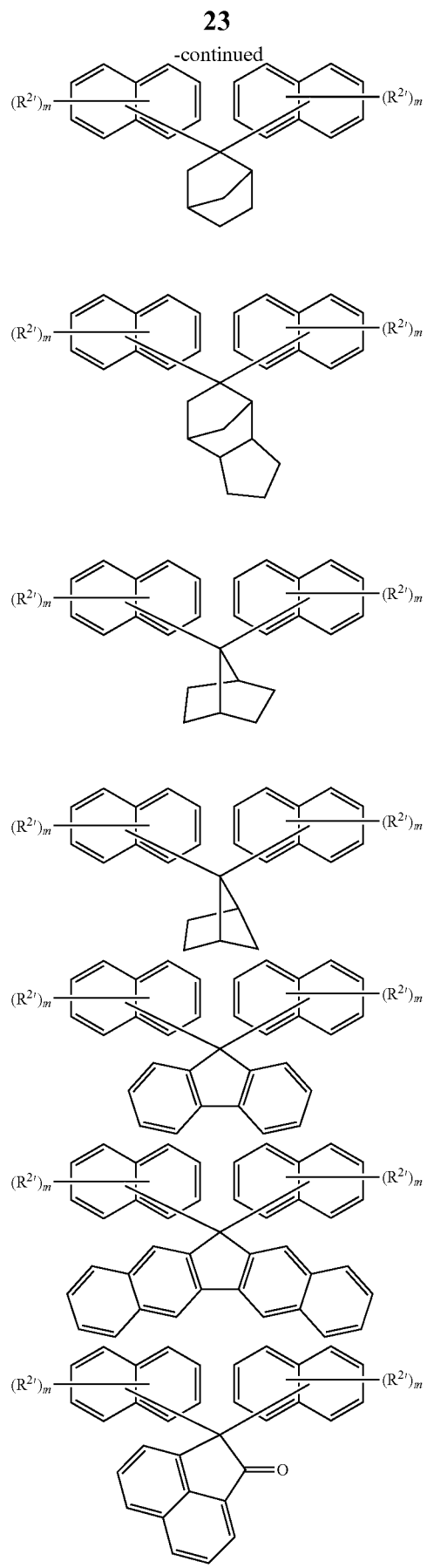
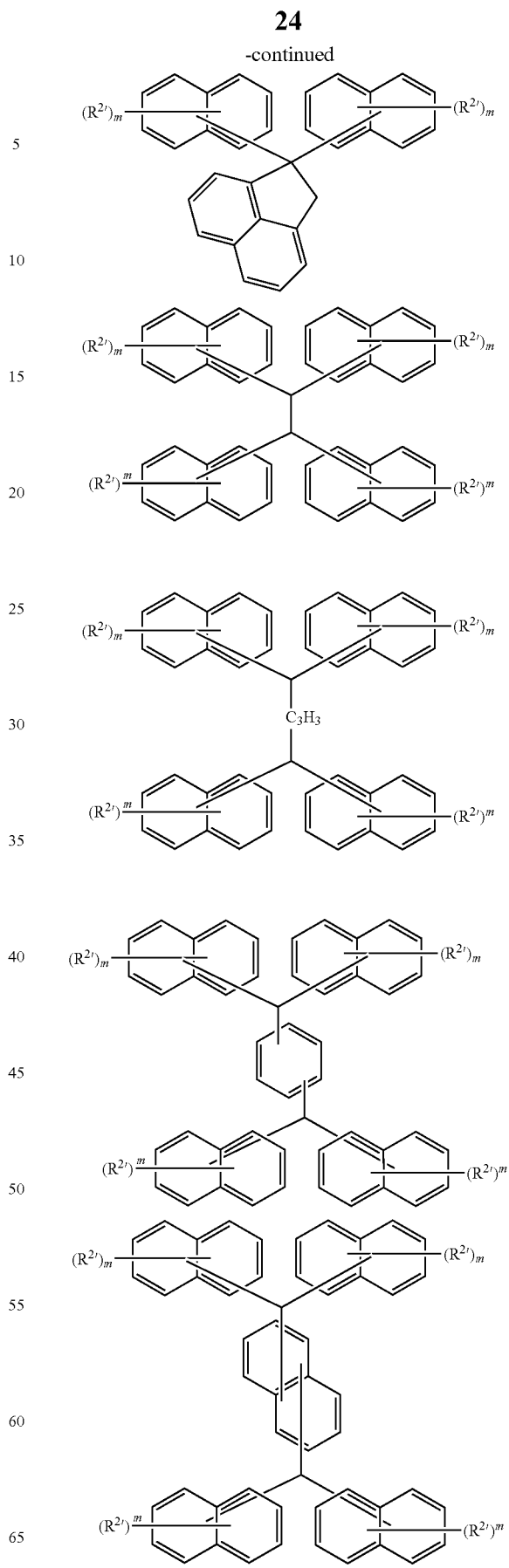

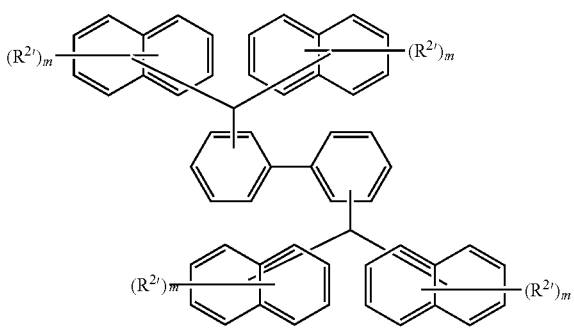

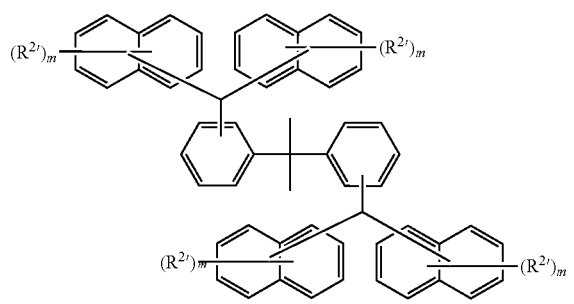

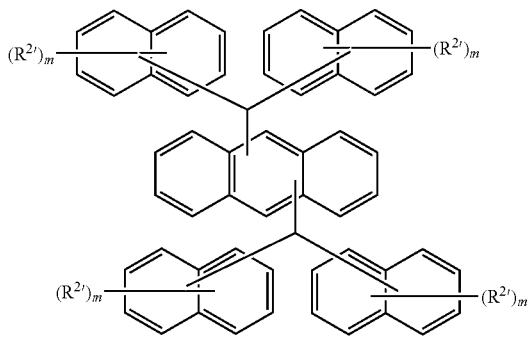

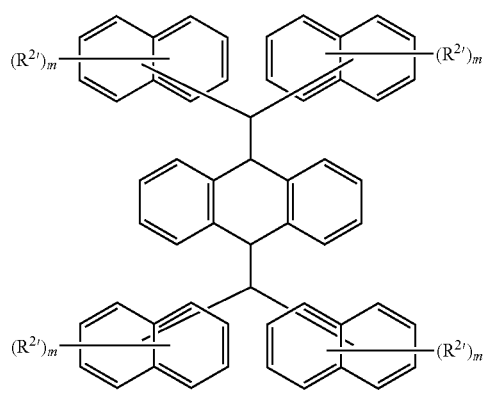

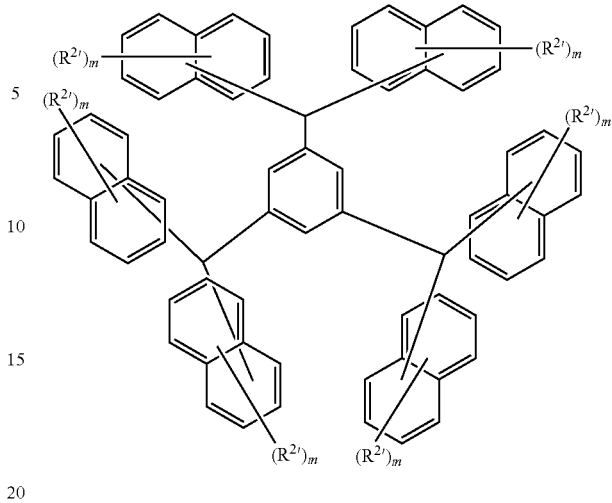

In the above formulae, $R^{2\prime}$ is the same as $R^2$ defined in the description of the above general formula (1), m is the same as $m^1$ defined in the description of the above general formula (1), and at least one $R^{2\prime}$ is a monovalent group containing an iodine atom.

In the present embodiment, a method for producing the compound represented by the above general formula (1) is not particularly limited. For example, the compound represented by the above general formula (1) wherein q=1 is obtained by reacting a naphthol or a thionaphthol with a corresponding aldehyde or ketone in the presence of an acid catalyst to obtain a polyphenol compound, and introducing an acid dissociation group to at least one phenolic hydroxy group of the obtained polyphenol compound by a publicly known method. The compound represented by the above general formula (1) wherein q=0 is not particularly limited, and can be similarly synthesized by, for example, using the naphthol or the thionaphthol in combination with a phenol or a thiophenol.

Examples of the naphthol include, but not particularly limited to, naphthol, methylnaphthol, methoxynaphthol, and naphthalenediol. Naphthalenediol is more preferably used because a xanthene structure can be easily made.

Examples of the thionaphthol include, but not particularly limited to, naphthalenethiol, methylnaphthalenethiol, methoxynaphthalenethiol, and naphthalenedithiol.

Examples of the phenol include, but not particularly limited to, phenol, methylphenol, methoxybenzene, catechol, resorcinol, hydroquinone, and trimethylhydroquinone.

Examples of the thiophenol include, but not particularly limited to, benzenethiol, methylbenzenethiol, methoxybenzenethiol, benzenedithiol, and trimethylbenzenedithiol.

Examples of the aldehyde include, but not particularly limited to, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane, and benzenetricarboxaldehyde. Benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl) methane, bis(diformylphenyl)propane, or benzenetricarboxaldehyde is preferably used in terms of providing high heat resistance.

Examples of the ketone are not particularly limited and include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, and cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used in terms of providing high heat resistance.

The above acid catalyst is not particularly limited and can be arbitrarily selected from well-known inorganic acids and organic acids. Examples include inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. From the viewpoint of production such as easy availability and handleability, hydrochloric acid or sulfuric acid is preferably used. As the acid catalyst, one kind or two or more kinds can be used.

When producing the compound represented by the above general formula (1), a reaction solvent may be used. The reaction solvent is not particularly limited as long as the reaction of the aldehyde or the ketone used with the naphthol or the thionaphthol proceeds. For example, water, methanol, ethanol, propanol, butanol, tetrahydrofuran, dioxane, or a mixed solvent thereof can be used. The amount of the reaction solvent used is not particularly limited and is within the range of, for example, 0 to 2000 parts by mass based on 100 parts by mass of the reaction raw materials.

When producing the above polyphenol compound, the reaction temperature is not particularly limited and can be arbitrarily selected according to the reactivity of the reaction raw materials. The reaction temperature is preferably within the range of 10 to 200° C. For highly selectively synthesizing the compound represented by the above general formula (1) used in the present embodiment, a lower reaction temperature is more effective, and the range of 10 to 60° C. is more preferable.

Examples of the method for producing the above polyphenol compound include, but not particularly limited to, a method of charging the naphthol or thionaphthol, the aldehyde or ketone, and the acid catalyst at once, and a method of dropping the naphtholor or thionaphthol and the aldehyde or ketone in the presence of the acid catalyst. After the polycondensation reaction terminates, the temperature of the reaction vessel is elevated to 130 to 230° C. in order to remove unreacted raw materials and acid catalyst, etc. present in the system, and volatile components can also be removed at about 1 to 50 mmHg.

When producing the above polyphenol compound, the amounts of raw materials are not particularly limited. For example, 2 mol to an excess of the naphthol or thionaphthol, the aldehyde or ketone and 0.001 to 1 mol of the acid catalyst based on 1 mol of the aldehyde or ketone are used, and the polycondensation reaction proceeds by reacting at 20 to 60° C. at normal pressure for about 20 minutes to 100 hours.

When producing the above polyphenol compound, the target component is isolated by a publicly known method after the reaction terminates. The method for isolating the target component is not particularly limited. An exemplary method involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the objective compound.

The method for introducing an acid dissociation group to at least one phenolic hydroxy group of the polyphenol compound is publicly known. For example, an acid dissociation group can be introduced to at least one phenolic hydroxy group of the polyphenol compound as described below. The compound for introducing an acid dissociation group may be synthesized by a publicly known method or may be obtained as a commercially available product. Examples include, but not particularly limited to, active carboxylic acid derivatives such as acid chloride, acid anhydride, and dicarbonate, alkyl halide, vinyl alkyl ether, dihydropyran, and halocarboxylic acid alkyl ester.

For example, the polyphenol compound is dissolved or suspended in an aprotic solvent such as acetone, tetrahydrofuran (THF), and propylene glycol monomethyl ether acetate. Subsequently, a vinyl alkyl ether such as ethyl vinyl ether, or dihydropyran, is added and reacted at 20 to 60° C. at normal pressure for 6 to 72 hours in the presence of an acid catalyst such as pyridinium p-toluenesulfonate. The reaction solution is neutralized with an alkali compound and added to distilled water to precipitate white solids, and the separated white solids can then be washed with distilled water and dried to obtain the compound represented by the above general formula (1).

Alternatively, for example, the polyphenol compound is dissolved or suspended in an aprotic solvent such as acetone, THF, and propylene glycol monomethyl ether acetate. An alkyl halide such as ethyl chloromethyl ether or a halocarboxylic acid alkyl ester such as methyladamantyl bromoacetate is added and reacted at 20 to 110° C. at normal pressure for 6 to 72 hours in the presence of an alkali catalyst such as potassium carbonate. The reaction solution is neutralized with an acid such as hydrochloric acid and added to distilled water to precipitate white solids, and the separated white solids can then be washed with distilled water and dried to obtain the compound represented by the above general formula (1).

In the present embodiment, the acid dissociation group refers to a characteristic group that is cleaved in the presence of an acid, thereby providing a functional group changing the solubility of an alkali soluble group or the like. Examples of the alkali soluble group include, but not particularly limited to, a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The above acid dissociation group preferably has the property of causing chain cleavage reactions in the presence of an acid in order to achieve higher sensitivity and higher resolution pattern formation.

(Resist Composition of Second Embodiment)

The second embodiment of the resist composition of the present embodiment contains a compound represented by the following general formula (2).

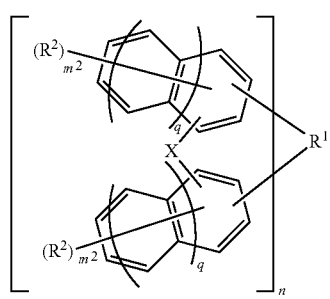

(2)

In the above general formula (2), each X is independently an oxygen atom or a sulfur atom, and $R^1$ is a single bond or a C1-30 2n-valent group. Herein, the C1-30 2n-valent group may have an alicyclic hydrocarbon group, a double bond, a hetero atom, or a C6-30 aromatic group. In general formula (2), each $R^2$ is independently a halogen atom, a C1-10 linear, branched, or cyclic alkyl group, a C6-10 aryl group, a C2-10 alkenyl group, a hydroxy group, or a group obtained by replacing a hydrogen atom of a hydroxy group with an acid dissociation group, and may be the same or different on the same naphthalene ring or benzene ring; each $m^2$ is independently an integer of 0 to 6, provided that at least one $m^2$ is an integer of 1 to 6; n is an integer of 1 to 4, and when n is an integer of 2 or greater in the general formula (2), structural formulae of n repeating units may be the same or different. In the general formula (2), at least one $R^2$ is a group obtained by replacing a hydrogen atom of a hydroxy group with an acid dissociation group, and at least one selected from the group consisting of $R^1$ and $R^2$ is a group containing an iodine atom.

The "at least one selected from the group consisting of $R^1$ and $R^3$" means "at least one group selected from the group consisting of $R^1$ and $R^3$", and does not mean "at least one kind of group selected from the group consisting of $R^1$ and $R^3$".

In the general formula (2), q is 0 or 1, and is preferably q=1. That is to say, the compound represented by the above general formula (2) is preferably a compound represented by the following general formula (2-a).

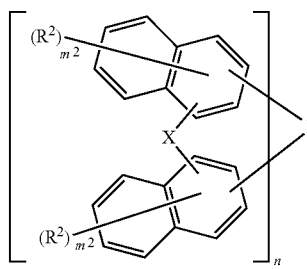

(2-a)

In the above general formula (2-a), $R^1$, $R^2$, n, and $m^2$ are as defined in the above general formula (2).

In the compound represented by the above general formula (2), X is preferably an oxygen atom in terms of suppression of device contamination during resist film exposure, and in terms of solubility in a safe solvent and resist pattern characteristics, the compound represented by the following formula (2-1) is preferable.

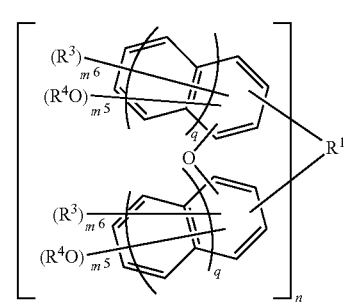

(2-1)

In the above general formula (2-1), $R^1$, $R^3$, $R^4$, n, and q are as defined in the above general formula (1-1), each $m^5$ is independently an integer of 1 to 6; each $m^6$ is independently an integer of 0 to 5, and $m^5+m^6$ is an integer of 1 to 6.

In the above general formula (2-1), q is 0 or 1, and q is preferably 1. That is to say, the compound represented by the above general formula (2) is more preferably a compound represented by the following formula (2-1-a).

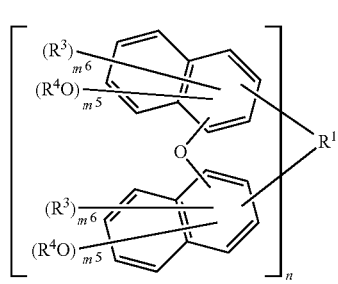

(2-1-a)

In the above general formula (2-1-a), $R^1$, $R^3$, $R^4$, n, $m^5$, and $m^6$ are as defined in the above general formula (2-1).

In terms of sensitivity when formed into a resist composition, the compound represented by the above general formula (2-1) is more preferably a compound represented by the following general formula (2-2).

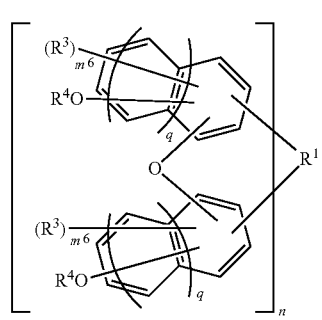

(2-2)

In the above general formula (2-2), $R^1$, $R^3$, $R^4$, $m^6$, n, and q are as defined in the above formula (2-1).

In the above general formula (2-2), q is more preferably 1. That is to say, the compound represented by the above general formula (2) is more preferably a compound represented by the following general formula (2-2-a).

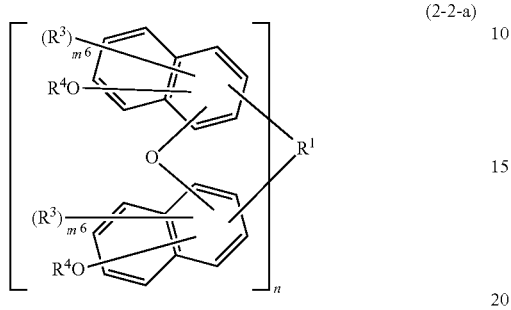
(2-2-a)

In terms of solubility, and sensitivity when formed into a resist composition, $m^5$ is preferably 2 in the above general formula (2-1).

In terms of resist characteristics such as heat resistance, sensitivity, resolution, and roughness in the present embodiment, the compound represented by the above general formula (2-1) is preferably a compound of the above general formula (2-1) wherein n is 1.

In terms of solubility, the compound represented by the above general formula (2) is more preferably a compound represented by the following general formula (2-3) in the present embodiment.

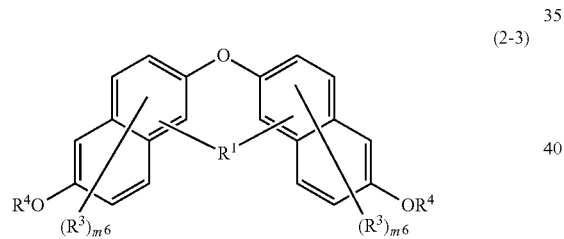
(2-3)

In the above general formula (2-3), $R^1$, $R^3$, $R^4$, and $m^6$ are as defined in the above general formula (2-1).

Specific examples of the compound represented by the above general formula (2) can include, but not limited to, the followings.

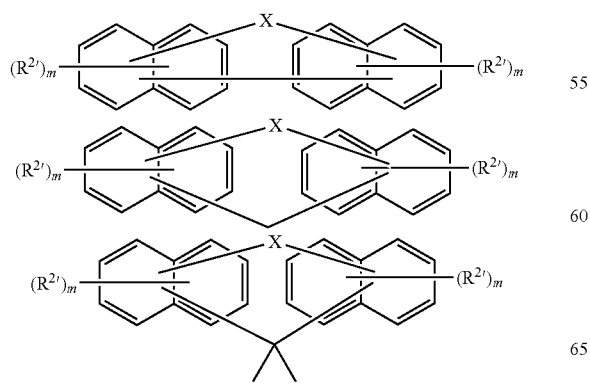

-continued

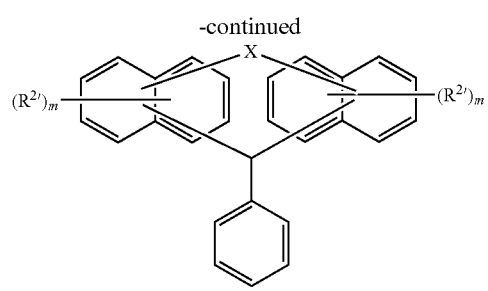

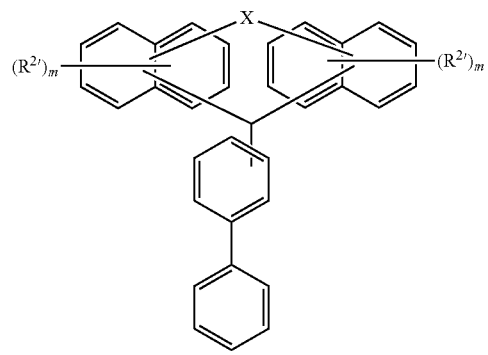

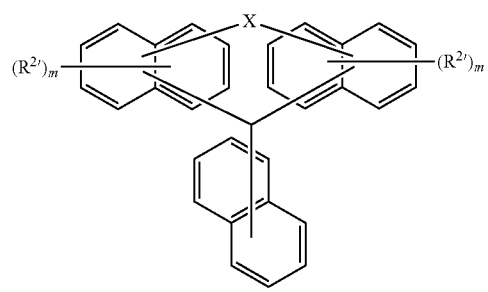

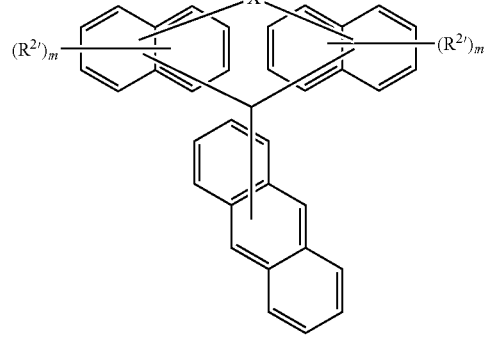

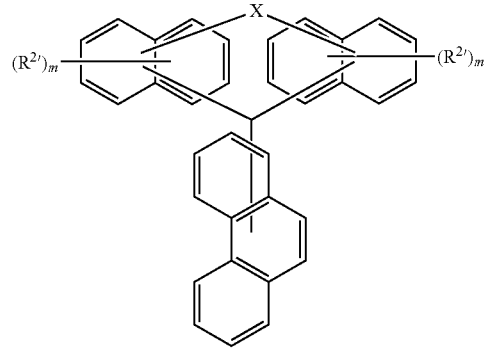

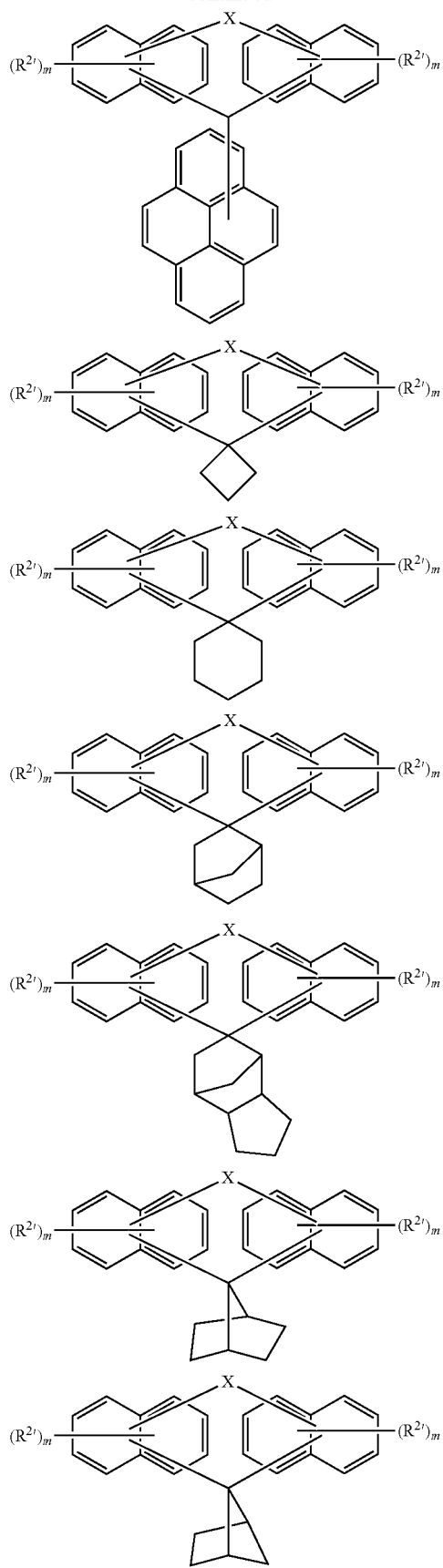
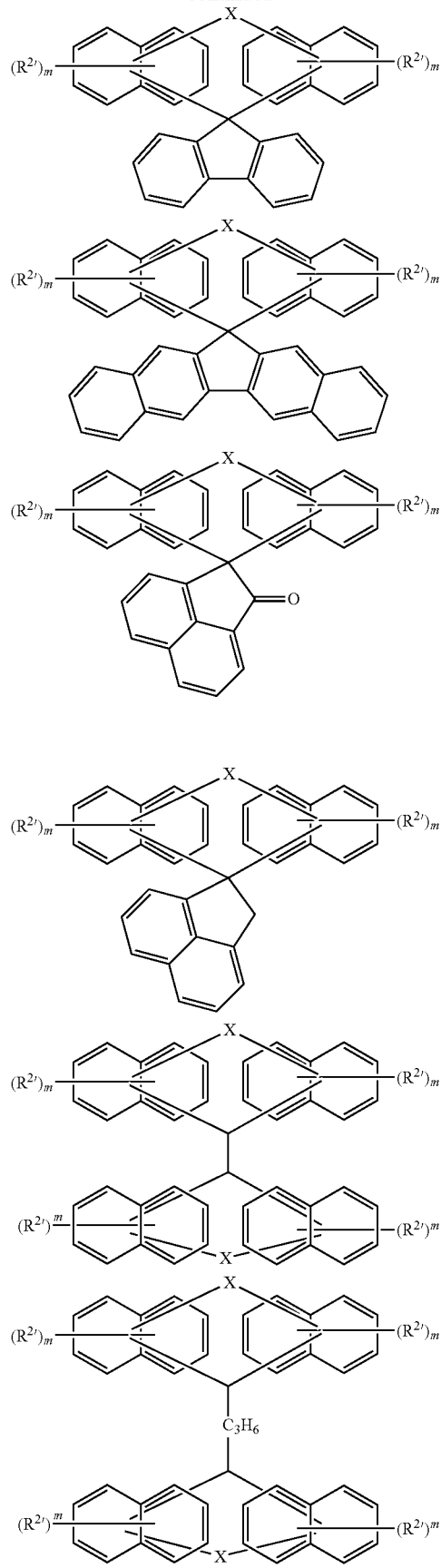

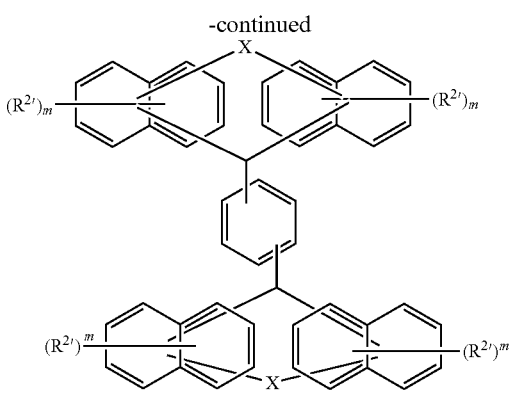

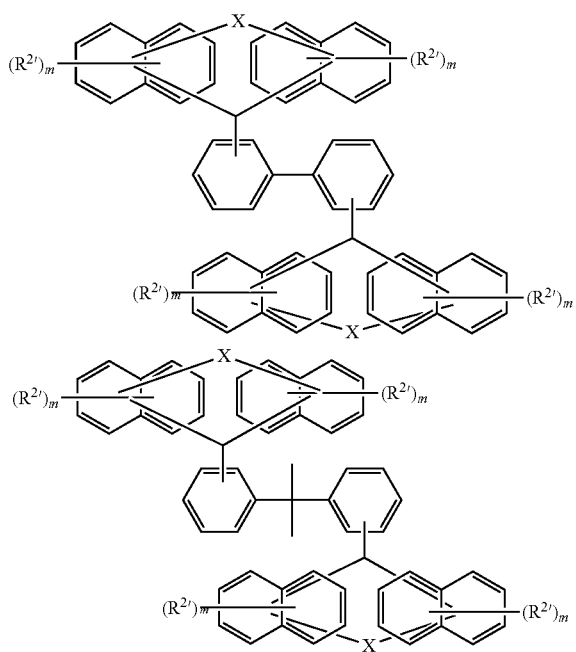

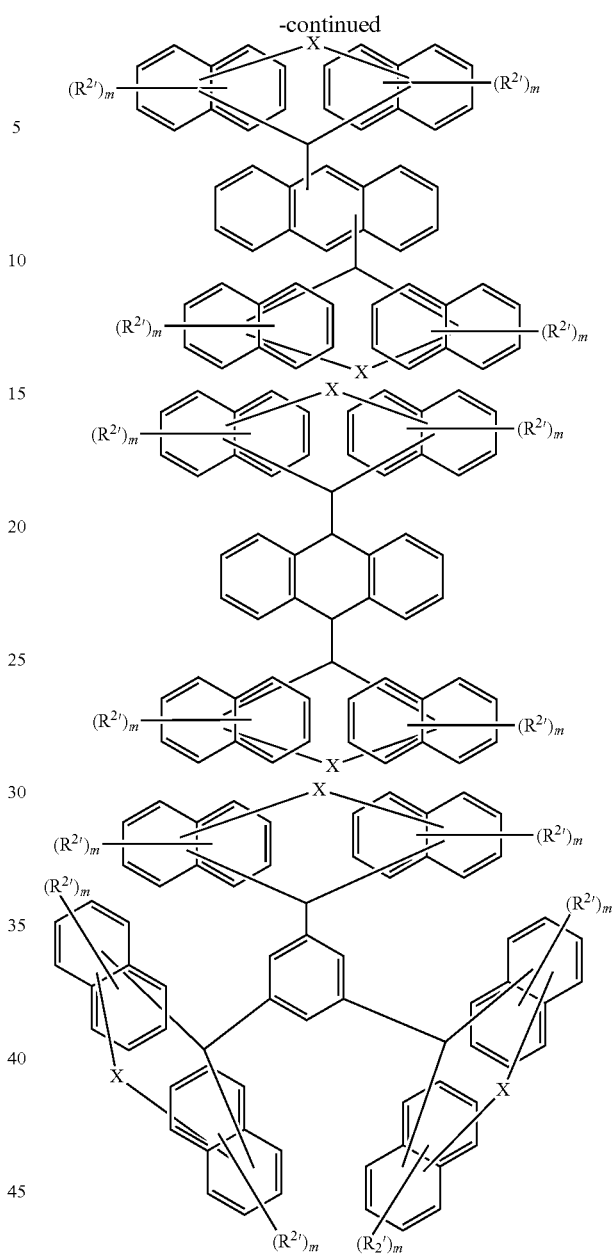

In the above formulae, X is the same as in the above general formula (2), and $R^{2'}$ is the same as $R^2$ defined in the description of the above general formula (2), m is the same as $m^2$ defined in the description of the above general formula (2), and at least one $R^{2'}$ is a monovalent group containing an iodine atom.

As with the compound represented by the above general formula (1), the compound represented by the above general formula (2) wherein q=1 is obtained by, for example, reacting a naphthol or a thionaphthol with a corresponding aldehyde or ketone in the presence of an acid catalyst to obtain a polyphenol compound, and introducing an acid dissociation functional group to at least one phenolic hydroxy group of the obtained polyphenol compound by a publicly known method. The compound represented by the above general formula (2) wherein q=0 is not particularly limited, and can be similarly synthesized by, for example, using the naphthol or the thionaphthol in combination with a phenol or a thiophenol.

[Compound]

The compound of the present embodiment is a compound represented by the above general formula (1) or (2). The compound represented by the above general formula (1) is preferably a compound represented by the above general formula (1-1), and is more preferably a compound represented by the above general formula (1-2). Also, the compound represented by the above general formula (2) is preferably a compound represented by the above general formula (2-1), and is more preferably a compound represented by the above general formula (2-2).

Moreover, it is particularly preferable that the compound of the present embodiment is a compound represented by the following general formula (3) or (4) (such as a polyphenol derivative).

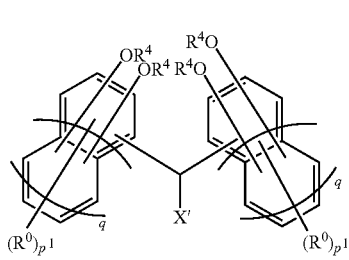
(3)

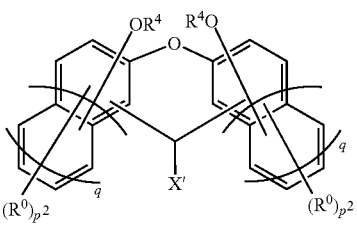
(4)

In the general formulae (3) and (4), X' is a hydrogen atom, a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; in the general formula (3), each $p^1$ is independently an integer of 0 to 5; in the general formula (4), each $p^2$ is independently an integer of 0 to 5; and in the general formulae (3) and (4), each q is independently 0 or 1; provided that in the general formulae (3) and (4), at least one $R^4$ is an acid dissociation group, and at least one selected from the group consisting of X' and $R^0$ is a group containing an iodine atom.

In the general formulae (3) and (4), X' is preferably a hydrogen atom, a halogen atom, or a monovalent hydrocarbon group of 1 to 18 carbon atoms.

The compounds represented by the above general formulae (3) and (4) (such as a polyphenol derivative) are preferably compounds represented by the following general formulae (3-1) and (4-1), respectively.

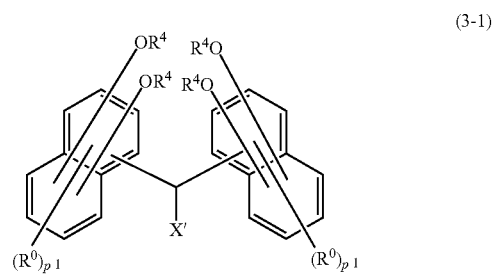
(3-1)

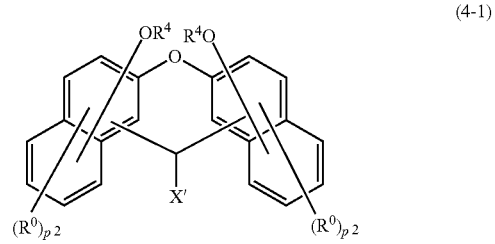
(4-1)

In the general formulae (3-1) and (4-1), wherein X' is a hydrogen atom, a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; in the general formula (3-1), each $p^1$ is independently an integer of 0 to 5; and in the general formula (4-1), each $p^2$ is independently an integer of 0 to 5; provided that in the general formulae (3-1) and (4-1), at least one $R^4$ is an acid dissociation group, and at least one selected from the group consisting of X' and $R^0$ is a group containing an iodine atom.

In the general formulae (3-1) and (4-1), X' is preferably a hydrogen atom, a halogen atom, or a monovalent hydrocarbon group of 1 to 18 carbon atoms.

Due particularly to having a naphthalene skeleton, the compound of the present embodiment (such as a polyphenol compound) exhibits the effect of having excellent heat resistance and, in addition to heat resistance, excellent solubility in a safe solvent.

The positions of hydroxy groups on the naphthalene ring are not particularly limited, but are preferably 1,5-positions, 1,6-positions, 1,7-positions, 2,3-positions, 2,7-positions, and 2,6-positions in terms of the industrial applicability of raw materials, and more preferably 2,6-positions in terms of even higher solubility in a safe solvent and low crystallinity.

It is particularly preferable that the resist composition of the present embodiment contains a compound represented by the above general formula (3) or (4) (such as a polyphenol derivative).

[Resin]

The resin of the present embodiment is a resin obtained using the compound represented by the above formula (1) or (2) as a monomer.

The resin of the present embodiment is obtained by, for example, reacting the compound represented by the above formula (1) or (2) with a crosslinking compound.

As the crosslinking compound, a publicly known monomer can be used without particular limitations as long as it can oligomerize or polymerize the compound represented by the above formula (1) or (2). Specific example thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

[Method for Purifying Compound or Resin]

The method for purifying the compound or the resin of the present embodiment comprises the steps of:

obtaining a solution (A) by dissolving one or more selected from the compound represented by the above general formula (1), the compound represented by the above general formula (2), and a resin obtained using these as monomers in a solvent; and extracting impurities in the compound or the resin by bringing the obtained solution (A) into contact with an acidic aqueous solution (a first extraction step), wherein the solvent used in the step of obtaining the solution (A) contains an organic solvent that does not inadvertently mix with water.

In the first extraction step, the resin is preferably a resin obtained by a reaction between the compound represented by the above formula (1) or (2) and a crosslinking compound.

Because the purification method of the present embodiment is configured as described above, according to the purification method, the contents of various metals that may be contained as impurities in the compound or the resin having a specific structure described above can be reduced.

More specifically, in the purification method of the present embodiment, the above compound or resin is dissolved in an organic solvent that does not inadvertently mix with water to obtain the solution (A), and further, extraction treatment can be carried out by bringing the solution (A) into contact with an acidic aqueous solution. Thereby, metals contained in the solution (A) containing the compound represented by the above general formula (1), the compound represented by the above general formula (2), or the resin obtained using these as monomers are transferred to the aqueous phase, then the organic phase and the aqueous phase are separated, and thus the compound represented by the above general formula (1), the compound represented by the above general formula (2), or the resin obtained using these as monomers with the reduced metal contents can be obtained.

The compound represented by the above general formula (1), the compound represented by the above general formula (2), or the resin obtained using these as monomers used in the purification method of the present embodiment may be alone, or may be a mixture of two or more kinds. Also, the compound represented by the above general formula (1), the compound represented by the above general formula (2), or the resin obtained using these as monomers may contain various surfactants, various crosslinking agents, various acid generators, various stabilizers, and the like.

The organic solvent that does not inadvertently mix with water used in the purification method of the present embodiment is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 times the mass of the compound represented by the above general formula (1), the compound represented by the above general formula (2), or the resin obtained using these as monomers.

Specific examples of the organic solvent that does not inadvertently mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone (CHN), cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the compound represented by the above general formula (1), the compound represented by the above general formula (2), or the resin obtained using these as monomers and a relatively low boiling point, and it is thus possible to reduce the load in the case of industrially distilling off the solvent and in the step of removing the solvent by drying.

These organic solvents can be each used alone, and can be used as a mixture of two or more kinds.

The acidic aqueous solution used in the purification method of the present embodiment is arbitrarily selected from aqueous solutions in which generally known organic compounds or inorganic compounds are dissolved in water. Examples include, but not limited to, aqueous mineral acid solutions in which mineral acids such as hydrochloric acid, sulfuric acid, nitric acid, and phosphoric acid are dissolved in water; and aqueous organic acid solutions in which organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound represented by the above general formula (1), the compound represented by the above general formula (2), or the resin obtained using these as monomers. Normally, the pH range is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (A).

In the purification method of the present embodiment, by bringing an acidic aqueous solution as described above into contact with the solution (A) containing one or more selected from the compound represented by the above general formula (1), the compound represented by the above general formula (2), and the resin obtained using these as monomers, and an organic solvent that does not inadvertently mixes with water, metals can be extracted from the compound or the resin in the solution (A).

In the purification method of the present embodiment, it is preferable that the solution (A) further contains an organic solvent that advertently mixes with water. When an organic solvent that advertently mixes with water is contained, there is a tendency that the amount of the compound represented by the above general formula (1), the compound represented by the above general formula (2), or the resin obtained using these as monomers charged can be increased, also the fluid separability is improved, and purification can be carried out at a high reaction vessel efficiency. The method for adding the organic solvent that advertently mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solution phase and the aqueous phase separate, but is preferably 0.1 to 100 times, more preferably 0.1 to 50 times, and further preferably 0.1 to 20 times the mass of the compound represented by the above general formula (1), the compound represented by the above general formula (2), and the resin obtained using these as monomers.

Specific examples of the organic solvent used in the purification method of the present embodiment that inadvertently mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

In the purification method of the present embodiment, the temperature when the solution (A) and the acidic aqueous solution are brought into contact, i.e., when extraction treatment is carried out, is preferably in the range of 20 to 90° C., and more preferably 30 to 80° C. The extraction operation is not particularly limited, and is carried out, for example, by thoroughly mixing the solution (A) and the acidic aqueous solution by stirring or the like and then leaving the obtained mixed solution to stand still. Thereby, metals contained in the solution (A) containing organic solvents and one or more selected from the compound represented by the above general formula (1), the compound represented by the above general formula (2), and the resin obtained using these as monomers are transferred to the aqueous phase. Also, by this operation, the acidity of the solution (A) is lowered, and the degradation of the compound represented by the above general formula (1), the compound represented by the above general formula (2), and the resin obtained using these as monomers can be suppressed.

By being left to stand still, the mixed solution is separated into an aqueous phase and a solution phase containing the organic solvents and one or more selected from the compound represented by the above general formula (1), the compound represented by the above general formula (2), and the resin obtained using these as monomers, and thus the solution phase containing the organic solvents and one or more selected from the compound represented by the above general formula (1), the compound represented by the above general formula (2), and the resin obtained using these as monomers is recovered by decantation or the like. The time for leaving the mixed solution to stand still is not particularly limited, but it is preferable to regulate the time for leaving the mixed solution to stand still from the viewpoint of attaining good separation of the solution phase containing the organic solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step). Specifically, for example, it is preferable that after the above extraction treatment is carried out using an acidic aqueous solution, the solution phase that is extracted and recovered from the aqueous solution and that contains the organic solvents and one or more selected from the compound represented by the above general formula (1), the compound represented by the above general formula (2), and the resin obtained using these as monomers is further subjected to extraction treatment with water. The above extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing the organic solvents and one or more selected from the compound represented by the above general formula (1), the compound represented by the above general formula (2), and the resin obtained using these as monomers, and thus the solution phase containing the organic solvents and one or more selected from the compound represented by the above general formula (1), the compound represented by the above general formula (2), and the resin obtained using these as monomers can be recovered by decantation or the like.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing the organic solvents and one or more selected from the compound represented by the above general formula (1), the compound represented by the above general formula (2), and the resin obtained using these as monomers can be easily removed by performing vacuum distillation or a like operation. Also, if required, the concentration of the compound represented by the above general formula (1), the compound represented by the above general formula (2), and the resin obtained using these as monomers can be regulated to be any concentration by adding an organic solvent to the solution.

The method for isolating the one or more selected from the compound represented by the above general formula (1), the compound represented by the above general formula (2), and the resin obtained using these as monomers from the obtained solution containing the organic solvents and one or more selected from the compound represented by the above general formula (1), the compound represented by the above general formula (2), and the resin obtained using these as monomers is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

(Physical Properties and the Like of Resist Composition)

The resist composition of the present embodiment can form an amorphous film by spin coating. Depending on the kind of the developing solution used, any of a positive type resist pattern and a negative type resist pattern can be selectively prepared.

In the case of a positive type resist pattern, the dissolution rate of the amorphous film formed by spin coating with the resist composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the amorphous film is insoluble in a developing solution and can form a resist. When the amorphous film has a dissolution rate of 0.0005 angstrom/sec or more, the resolution may improve. It is presumed that this is because due to the change in the solubility before and after exposure of the compound represented by the above general formula (1) or (2), contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the resist composition of the present embodiment in a developing solution at 23° C. is preferably 10 angstrom/sec or more. When the dissolution rate is 10 angstrom/sec or more, the amorphous film easily dissolves in a developing solution, and is more suitable for a resist. When the amorphous film has a dissolution rate of 10 angstrom/sec or more, the resolution may improve. It is presumed that this is because the micro surface portion of the compound represented by the above general formula (1) or (2) dissolves and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C., is preferably 10 angstrom/sec or more. When the dissolution rate is 10 angstrom/sec or more, the above portion is easily soluble in a developing solution, and thus the amorphous film is more suitable for a resist. When the amorphous film has a dissolution rate of 10 angstrom/sec or more, the resolution may improve. It is presumed that this is because the micro surface portion of the compound represented by the above general formula (1) or (2) dissolves and LER is reduced. Also, there are effects of reducing defects.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C., is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above general formula (1) or (2), contrast at the interface between the unexposed portion being dissolved in a developing solution and the exposed portion not being dissolved in a developing solution is increased. Also, there are effects of reducing LER and defects.

(Other Components of Resist Composition)

The resist composition of the present embodiment contains the compound represented by the above general formula (1) or the compound represented by the above general formula (2) as a solid component. The resist composition of the present embodiment may contain both the compound represented by the above general formula (1) and the compound represented by the above general formula (2).

It is preferable that the resist composition of the present embodiment further contains a solvent other than the compound represented by the above general formula (1) or (2).

Examples of the solvent used in the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate (PGMEA), propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as methyl ethyl ketone, 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the resist composition of the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the resist composition of the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the solid component and the solvent.

The resist composition of the present embodiment may contain at least one selected from the group consisting of an acid generating agent (C), an acid diffusion controlling agent (E), and a further component (F), as other solid components.

In the resist composition of the present embodiment, the content of the compound represented by the above general formula (1) and/or the compound represented by the above general formula (2) is not particularly limited, but is preferably 50 to 99.4% by mass of the total mass of the solid components (summation of the compound represented by the formula (1) and the compound represented by the formula (2), and optionally used solid components such as acid generating agent (C), acid diffusion controlling agent (E), and further component (F), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased.

When both the compound represented by the above general formula (1) and the compound represented by the above general formula (2) are contained, the content refers to the total amount of the compound represented by the above general formula (1) and the compound represented by the above general formula (2).

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam.

In this case, in the resist composition of the present embodiment, the content of the acid generating agent (C) is preferably 0.001 to 49% by mass of the total mass of the solid components, more preferably 1 to 40% by mass, still more preferably 3 to 30% by mass, and particularly preferably 10 to 25% by mass. By using the acid generating agent (C) within the above content range, a pattern profile with even higher sensitivity and even lower edge roughness is obtained.

Concerning the resist composition of the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is not particularly limited, and is preferably at least one kind selected from the group consisting of compounds represented by the following formulae (8-1) to (8-8):

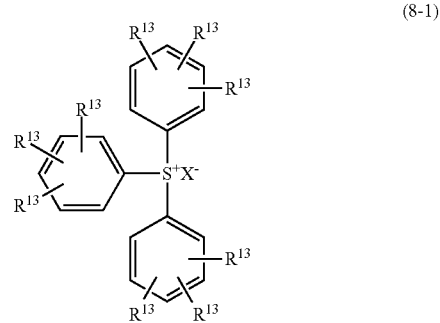

(8-1)

(In the formula (8-1), $R^{13}$ may be the same or different, and are each independently a hydrogen atom, a linear, branched or cyclic alkyl group, a linear, branched or cyclic alkoxy group, a hydroxyl group, or a halogen atom, $X^-$ is an alkyl group, an aryl group, a sulfonic acid ion having a halogen substituted alkyl group or a halogen substituted aryl group, or a halide ion.)

The compound represented by the above formula (8-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4, 6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

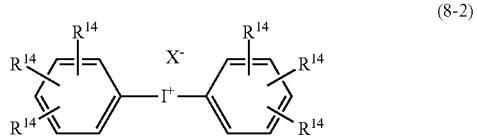

(8-2)

(In the formula (8-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.)

The compound represented by the above formula (8-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

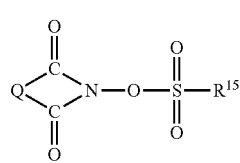

(8-3)

(In the formula (8-3), Q is an alkylene group, an arylene group, or an alkoxylene group, and $R^{15}$ is an alkyl group, an aryl group, a halogen substituted alkyl group, or a halogen substituted aryl group.)

The compound represented by the above formula (8-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2,2,1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, camphorsulfonyloxy)diphenylmaleimide, N-(10-camphorsulfonyloxy)bicyclo[2,2,1]hept-5-en-2,3-dicarboxyimide, N-(10-camphorsulfonyloxy)naphthylimide, N-(n-octanesulfonyloxy)bicyclo[2,2,1]hept-5-en-2,3-dicarboxyimide, N-(n-octanesulfonyloxy)naphthylimide, N-(p-toluenesulfonyloxy)bicyclo[2,2,1]hept-5-en-2,3-dicarboxyimide, N-(p-toluenesulfonyloxy)naphthylimide, N-(2-trifluoromethylbenzenesulfonyloxy)bicyclo[2,2,1]hept-5-en-2,3-dicarboxyimide, N-(2-trifluoromethylbenzenesulfonyloxy)naphthylimide, N-(4-trifluoromethylbenzenesulfonyloxy)bicyclo[2,2,1]hept-5-en-2,3-dicarboxyimide, N-(4-trifluoromethylbenzenesulfonyloxy)naphthylimide, N-(perfluorobenzenesulfonyloxy)bicyclo[2,2,1]hept-5-en-2,3-dicarboxyimide, N-(perfluorobenzenesulfonyloxy)naphthylimide, N-(1-naphthalenesulfonyloxy)bicyclo[2,2,1]hept-5-en-2,3-dicarboxyimide, N-(1-naphthalenesulfonyloxy)naphthylimide, N-(nonafluoro-n-butanesulfonyloxy)bicyclo[2,2,1]hept-5-en-2,3-dicarboxyimide, N-(nonafluoro-n-butanesulfonyloxy)naphthylimide, N-(perfluoro-n-octanesulfonyloxy)bicyclo[2,2,1]hept-5-en-2,3-dicarboxyimide, and N-(perfluoro-n-octanesulfonyloxy)naphthylimide.

(8-4)

(In the formula (8-4), $R^{16}$ may be the same or different, and are each independently an optionally substituted linear, branched or cyclic alkyl group, an optionally substituted aryl group, an optionally substituted heteroaryl group, or an optionally substituted aralkyl group.)

The compound represented by the above formula (8-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

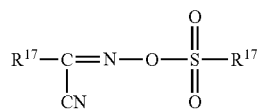

(8-5)

(In the formula (8-5), $R^{17}$ may be the same or different, and are each independently an optionally substituted linear, branched or cyclic alkyl group, an optionally substituted aryl group, an optionally substituted heteroaryl group, or an optionally substituted aralkyl group.)

The compound represented by the above formula (8-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

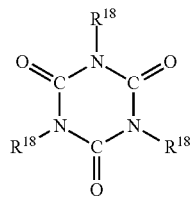

(8-6)

In the formula (8-6), $R^{18}$ may be the same or different, and are each independently a halogenated alkyl group having one or more chlorine atoms and one or more bromine atoms. The number of carbons in the halogenated alkyl group is preferably 1 to 5.

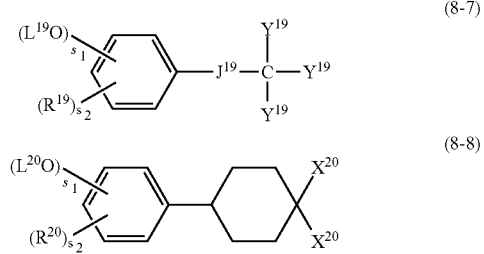

In the formulae (8-7) and (8-8), $R^{19}$ and $R^{20}$ are each independently a C1-3 alkyl group such as a methyl group, an ethyl group, an n-propyl group, and an isopropyl group; a cycloalkyl group such as a cyclopentyl group and a cyclohexyl group; a C1-3 alkoxyl group such as a methoxy group, an ethoxy group, and a propoxy group; or an aryl group such as a phenyl group, a toluoyl group, and a naphthyl group, and preferably a C6-10 aryl group. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. $S_1$ is an integer of 1 to 3; $S_2$ is an integer of 0 to 4; and $1 \leq S_1+S_2 \leq 5$. $J^{19}$ is a single bond, a C1-4 polymethylene group, a cycloalkylene group, a phenylene group, a group represented by the following formula (8-7-1), a carbonyl group, an ester group, an amide group, or an ether group. $Y^{19}$ is a hydrogen atom, an alkyl group, or an aryl group, and $X^{20}$ are each independently a group represented by the following formula (8-8-1):

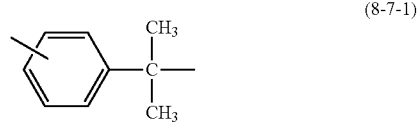

(8-7-1)

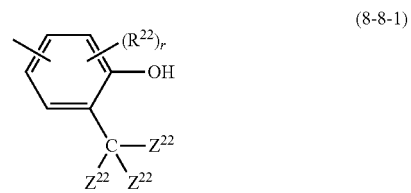

(8-8-1)

(In the above formula (8-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.)

Examples of the other acid generating agent include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, an acid generating agent having an aromatic ring is preferable, and an acid generating agent represented by the formula (8-1) or (8-2) is more preferable. An acid generating agent having a sulfonate ion wherein $X^-$ of the formula (8-1) or (8-2) has an aryl group or a halogen-substituted aryl group is more preferable; an acid generating agent having a sulfonate ion wherein $X^-$ of the formula (8-1) or (8-2) has an aryl group is particularly preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are particularly preferable. By using the acid generating agent, LER can be reduced.

The acid generating agent (C) can be used alone or in combination of two or more kinds.

The resist composition of the present embodiment may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the further improvement of the resolution, the line width change of a resist pattern due to variation in the post exposure delay time before radiation irradiation and the post exposure delay time after radiation irradiation can be inhibited, and the composition has extremely excellent process stability.

Such an acid diffusion controlling agent (E) is not particularly limited, and examples include a radiation degradable basic compound such as a nitrogen atom-containing basic compound, a basic sulfonium compound, and a basic iodonium compound. The acid diffusion controlling agent (E) can be used alone or in combination of two or more kinds.

The above acid diffusion controlling agent is not particularly limited, and examples include a nitrogen-containing organic compound, and a basic compound degradable by exposure. The above nitrogen-containing organic compound is not particularly limited, and examples include a compound represented by the following formula (11):

(11)

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above formula (11), $R^{61}$, $R^{62}$, and $R^{63}$ represent a hydrogen atom, a linear, branched or cyclic alkyl group, an aryl group, or an aralkyl group independently from each other. The above alkyl group, aryl group, or aralkyl group may be non-substituted or may be substituted with a hydroxyl group or the like. Herein, the above linear, branched or cyclic alkyl group is not particularly limited, and examples include the one of C1-15, and preferably C1-10. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include the one of C6-12. Specific examples thereof include a phenyl group, a tolyl group, a xylyl group, a cumenyl group, and a 1-naphthyl group. Furthermore, the above aralkyl group is not particularly limited, and examples include the one of C7-19, and preferably C7-13. Specific examples thereof include a benzyl group, an α-methylbenzyl group, a phenethyl group, and a naphthylmethyl group.

The above nitrogen-containing compound (I) is not particularly limited, and specific examples include particularly mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, methyl-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

The above nitrogen-containing compound (II) is not particularly limited, and specific examples include particularly ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

The above nitrogen-containing compound (III) is not particularly limited, and specific examples include particularly polymers of polyethyleneimine, polyarylamine, and N-(2-dimethylaminoethyl)acrylamide.

The above amide group-containing compound is not particularly limited, and specific examples include particularly formamide, N-methylformamide, N,N-dimethylformamide, acetamide, N-methylacetamide, N,N-dimethylacetamide, propioneamide, benzamide, pyrrolidone, and N-methylpyrrolidone.

The above urea compound is not particularly limited, and specific examples include particularly urea, methylurea, 1,1-dimethylurea, 1,3-dimethylurea, 1,1,3,3-tetramethylurea, 1,3-diphenylurea, and tri-n-butylthiourea.

The above nitrogen-containing heterocyclic compound is not particularly limited, and specific examples include particularly imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2,2,2]octane.

The radiation degradable basic compound is not particularly limited, and examples can include a sulfonium compound represented by the general formula (12-1):

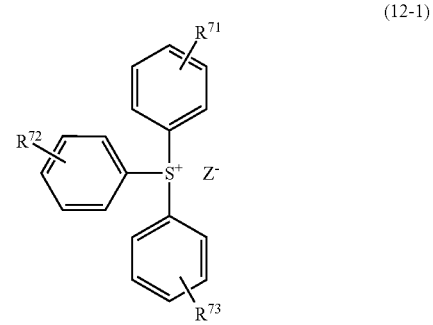

(12-1)

and an iodonium compound represented by the following formula (12-2):

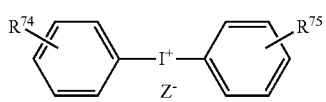
(12-2)

In the general formulae (12-1) and (12-2), $R^{71}$, $R^{72}$, $R^{73}$, $R^{74}$, and $R^{75}$ represent a hydrogen atom, a C1-6 alkyl group, a C1-6 alkoxyl group, a hydroxyl group, or a halogen atom independently from each other. $Z^-$ represents $HO^-$, $R-COO^-$ (R represents a C1-6 alkyl group, a C6-11 aryl group, or a C7-12 alkaryl group), or an anion represented by the following general formula (12-3):

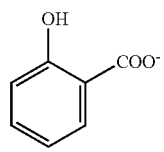
(12-3)

Specific examples of the above radiation degradable basic compound are not particularly limited, and examples include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl) iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total mass of the solid component, more preferably 0.01 to 10% by mass, still more preferably 0.01 to 5% by mass, and particularly preferably 0.01 to 3% by mass. When the content of the acid diffusion controlling agent (E) is within the above range, a decrease in resolution, and deterioration of the pattern shape and the dimension fidelity or the like can be further inhibited. Moreover, even though the post exposure delay time from electron beam irradiation to heating after radiation irradiation becomes longer, the shape of the pattern upper layer portion does not deteriorate. When the content of the acid diffusion controlling agent (E) is 10% by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition is extremely excellent process stability.

To the resist composition of the present embodiment, within the range of not inhibiting the purpose of the present embodiment, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof can be added.

(Dissolution Promoting Agent)

A low molecular weight dissolution promoting agent is a component having a function of increasing the solubility of the compound represented by the above formula (1) and/or the compound represented by the above formula (2) in a developing solution to moderately increase the dissolution rate of the compound upon developing, when the solubility of the compound is too low, and can be used within the range not impairing the effects of the present invention. Examples of the above dissolution promoting agent can include low molecular weight phenolic compounds, such as bisphenols and tris(hydroxyphenyl)methane. These dissolution promoting agents can be used alone or in mixture of two or more kinds. The content of the dissolution promoting agent, which is arbitrarily adjusted according to the kind of the compound represented by the above formula (1) and/or the compound represented by the above formula (2) to be used, is preferably 0 to 49% by mass of the total mass of the solid components, more preferably 0 to 5% by mass, still more preferably 0 to 1% by mass, and particularly preferably 0% by mass.

(Dissolution Controlling Agent)

The dissolution controlling agent is a component having a function of controlling the solubility of the compound represented by the above formula (1) and/or the compound represented by the above formula (2) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

The dissolution controlling agent is not particularly limited, and examples include aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent is not particularly limited and is arbitrarily adjusted according to the kind of the compound represented by the above formula (1) and/or the compound represented by the above formula (2) to be used, but is preferably 0 to 49% by mass of the total mass of the solid components, more preferably 0 to 5% by mass, still more preferably 0 to 1% by mass, and particularly preferably 0% by mass.

(Sensitizing Agent)

The sensitizing agent is a component having a function of absorbing irradiated radiation energy, transmitting the energy to the acid generating agent (C), and thereby increasing the acid production amount, and improving the apparent sensitivity of a resist. Such a sensitizing agent is not particularly limited, and examples include benzophenones, biacetyls, pyrenes, phenothiazines, and fluorenes. These sensitizing agents can be used alone or in two or more kinds. The content of the sensitizing agent, which is arbitrarily adjusted according to the kind of the compound represented by the above formula (1) and/or the compound represented by the above formula (2) to be used, is preferably 0 to 49% by mass of the total mass of the solid components, more preferably 0 to 5% by mass, still more preferably 0 to 1% by mass, and particularly preferably 0% by mass.

(Surfactant)

The surfactant is a component having a function of improving coatability and striation of the resist composition of the present embodiment, and developability of a resist or the like. Such a surfactant is not particularly limited, and may be any of anionic, cationic, nonionic or amphoteric. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant is not particularly limited and is arbitrarily adjusted according to the kind of the compound represented by the above formula (1) and/or the compound represented by the above formula (2) to be used, but is preferably 0 to 49% by mass of the total mass of the solid components, more preferably 0 to 5% by mass, still more preferably 0 to 1% by mass, and particularly preferably 0% by mass.

(Organic Carboxylic Acid or Oxo Acid of Phosphor or Derivative Thereof)

For the purpose of prevention of sensitivity deterioration or improvement of a resist pattern shape and post exposure delay stability or the like, and as an additional optional component, the resist composition of the present embodiment may contain an organic carboxylic acid or an oxo acid of phosphor or derivative thereof. The composition can be used in combination with the acid diffusion controlling agent, or may be used alone. The organic carboxylic acid is not particularly limited, and, for example, is suitably malonic acid, citric acid, malic acid, succinic acid, benzoic acid, salicylic acid, or the like. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound represented by the above formula (1) and/or the compound represented by the above formula (2) to be used, is preferably 0 to 49% by mass of the total mass of the solid components, more preferably 0 to 5% by mass, still more preferably 0 to 1% by mass, and particularly preferably 0% by mass.

(Other Additive Agent)

Furthermore, the resist composition of the present embodiment can contain one kind or two kinds or more of additive agents other than the above dissolution controlling agent, sensitizing agent, and surfactant, within the range of not inhibiting the purpose of the present invention, if required. Examples of such an additive agent include, but not particularly limited to, a dye, a pigment, and an adhesion aid. For example, the composition contains the dye or the pigment, and thereby a latent image of the exposed portion is visualized and influence of halation upon exposure can be alleviated, which is preferable. The composition contains the adhesion aid, and thereby adhesiveness to a substrate can be improved, which is preferable. Furthermore, examples of other additive agent can include, but not particularly limited to, a halation preventing agent, a storage stabilizing agent, a defoaming agent, and a shape improving agent. Specific examples thereof can include 4-hydroxy-4'-methylchalkone.

The total content of the optional component (F) is preferably 0 to 49% by mass of the total mass of the solid component, more preferably 0 to 5% by mass, still more preferably 0 to 1% by mass, and particularly preferably 0% by mass.

In the resist composition of the present embodiment, the content of the compound represented by the above formula (1) and/or the compound represented by the above formula (2), the acid generating agent (C), the acid diffusion controlling agent (E), and the optional component (F) (the compound represented by the formula (1) and/or the compound represented by the formula (2)/the acid generating agent (C)/the acid diffusion controlling agent (E)/the optional component (F)) is preferably 50 to 99.4/0.001 to 49/0.001 to 49/0 to 49 in % by mass based on the solid content, more preferably 55 to 90/1 to 40/0.01 to 10/0 to 5, still more preferably 60 to 80/3 to 30/0.01 to 5/0 to 1, and particularly preferably 60 to 70/10 to 25/0.01 to 3/0.

The content ratio of each component is selected from each range so that the summation thereof is 100% by mass. By the above content ratio, performance such as sensitivity, resolution, and developability is even better.

The method for purifying the resist composition of the present embodiment is not particularly limited, and, examples include a method involving dissolving each component in a solvent upon use into a homogenous solution, and then if required, filtering through a filter or the like with a pore diameter of about 0.2 μm, for example.

Examples of the solvent used in the preparation of the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. These solvents can be used alone or in combination of two or more kinds.

The resist composition of the present embodiment can contain a resin within the range of not inhibiting the purpose of the present invention. Examples of the resin include, but not particularly limited to, a novolac resin, polyvinyl phenols, polyacrylic acid, polyvinyl alcohol, a styrene-maleic anhydride resin, an acrylic acid, vinyl alcohol or vinylphenol as a monomeric unit, or derivative thereof. The content of the resin is not particularly limited and is arbitrarily adjusted according to the kind of the compound represented by the above formula (1) and/or the compound represented by the above formula (2) to be used, but is preferably 30 parts by mass or less per 100 parts by mass of the compound, more preferably 10 parts by mass or less, still more preferably 5 parts by mass or less, and particularly preferably 0 part by mass.

[Resist Pattern Formation Method]

A resist pattern formation method according to the present embodiment is not particularly limited, and a suitable method may be a method including steps of forming a resist film by coating a substrate with the above resist composition, exposing the formed resist film, and developing the exposed resist film to form a resist pattern.

The resist pattern of the present embodiment can also be formed as an upper layer resist in a multilayer process.

Specific examples of the resist pattern formation method include, but not particularly limited to, the following methods. A resist film is formed by coating a conventionally publically known substrate with the resist composition using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples are not particularly limited, and examples include a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic film and/or organic film provided thereon. Examples of the inorganic film include, but not particularly limited to, an inorganic antireflection film (inorganic BARC). Examples of the organic film include, but not particularly limited to, an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like.

In the resist pattern formation method of the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern is formed.

As the developing solution, a solvent having a solubility parameter (SP value) close to that of the compound represented by the above formula (1) and/or the compound represented by the above formula (2) to be used is preferably selected. A polar solvent such as a ketone-based solvent, an ester-based solvent, an alcohol-based solvent, an amide-based solvent, or an ether-based solvent; and a hydrocarbon-based solvent, or an alkaline aqueous solution can be used.

Depending on the kind of the developing solution, a positive type resist pattern or a negative type resist pattern can be selectively prepared. In general, in the case of a polar solvent such as a ketone-based solvent, an ester-based solvent, an alcohol-based solvent, an amide-based solvent, or an ether-based solvent, as well as a hydrocarbon-based solvent, a negative type resist pattern is obtained. In the case of an alkaline aqueous solution, a positive type resist pattern is obtained.

The ketone-based solvent is not particularly limited, and examples include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

The ester-based solvent is not particularly limited, and examples include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

The alcohol-based solvent is not particularly limited, and examples include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

The ether-based solvent is not particularly limited, and examples include dioxane and tetrahydrofuran in addition to the glycol ether-based solvents.

The amide-based solvent is not particularly limited, and examples can be used include N-methyl-2-pyrrolidone, N,N-dimethylacetamide, N,N-dimethylformamide, phosphoric hexamethyltriamide, and 1,3-dimethyl-2-imidazolidinone.

The hydrocarbon-based solvent is not particularly limited, and examples include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and even less than 50% by mass, more preferably less than 30% by mass, and further preferably less than 10% by mass. Particularly preferably, the developing solution is substantially moisture free. That is, the content of the organic solvent in the developing solution is not particularly limited, and is preferably 30% by mass or more and 100% by mass or less based on the total amount of the developing solution, preferably even 50% by mass or more and 100% by mass or less, more preferably 70% by mass or more and 100% by mass or less, further more preferably 90% by mass or more and 100% by mass or less, and particularly preferably 95% by mass or more and 100% by mass or less.

The alkaline aqueous solution is not particularly limited, and examples include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is not particularly limited, and examples are preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monomethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Further more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development are not particularly limited, and specific examples include a linear, branched or cyclic monohydric alcohol. Specific examples include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. Particularly preferable examples of monohydric alcohol having 5 or more carbon atoms include, but not limited to, 1-hexanol, 2-hexanol, 4-methyl-2-pentanol, 1-pentanol, and 3-methyl-1-butanol or the like can be used.

A plurality of these components may be mixed, or the component may be used by mixing the component with an organic solvent other than those described above.

The water content ratio in the rinsing solution is not particularly limited, and is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and much more preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include, but not particularly limited to, copper plating, solder plating, nickel plating, and gold plating.

The remaining resist pattern after etching can be peeled by an organic solvent. Examples of the above organic solvent are not particularly limited, and examples include PGMEA (propylene glycol monomethyl ether acetate), PGME (propylene glycol monomethyl ether), and EL (ethyl lactate). Examples of the above peeling method are not particularly limited, and examples include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

EXAMPLES

The present embodiment will be more specifically described with reference to examples below. However, the present invention is not limited to these examples.

Below, methods for measuring a compound and methods for evaluating resist performance and the like in examples are presented.

[Measurement Method]
(1) Structure of Compound

The structure of the compound was verified by carrying out $^1$H-NMR measurement under the following conditions using an Advance 600 II spectrometer manufactured by Bruker.
Frequency: 400 MHz
Solvent: d6-DMSO (other than Synthesis Example 4)
Internal standard: TMS
Measurement temperature: 23° C.
(2) Molecular Weight of Compound The molecular weight of the compound was measured using Agilent 5975/6890N manufactured by Agilent Corporation. Alternatively, the molecular weight was measured using Acquity UPLC/MALDI-Synapt HDMS manufactured by Water Corporation according to LC-MS analysis. Alternatively, the weight average molecular weight (Mw) and the number average molecular weight (Mn) in terms of polystyrene were determined by gel permeation chromatography (GPC) analysis to determine dispersibility (Mw/Mn).
Apparatus: Shodex Model GPC-101 (manufactured by Showa Denko K.K.)
Columns: KF-80M×3
Eluant: THF 1 ml/min
Temperature: 40° C.
(3) Metal Content of Compound The metal content of the compound was measured by ICP-MS analysis using ELAN DRC II manufactured by PerkinElmer.

[Evaluation Method]
(1) Safe Solvent Solubility Test of Compound

The solubilities of the compound in CHN, PGME, and PGMEA were evaluated according to the following criteria utilizing the amount of dissolution in each solvent. The amount of dissolution was measured at 23° C. by precisely weighing the compound into a test tube, adding a subject solvent so as to attain a predetermined concentration, applying ultrasonic waves for 30 minutes in an ultrasonic cleaner, and visually observing the subsequent state of the fluid.
  A: 5.0% by mass≤Amount of dissolution
  B: 3.0% by mass≤Amount of dissolution<5.0% by mass
  C: Amount of dissolution<3.0% by mass (2) Storage Stability and Thin Film Formability of Resist Composition The storage stability of a resist composition containing the compound was evaluated by leaving the resist composition to stand still for three days at 23° C. after preparation and then visually observing the resist composition for the presence and absence of precipitates. The resist composition after being left to stand still for 3 days was evaluated as ○ when it was a homogeneous solution and there were no precipitates, and x when there were precipitates. A clean silicon wafer was spin coated with the resist composition in a homogenous state, and then prebaked (PB) before exposure in an oven of 110° C. to form a resist film with a thickness of 40 nm. The prepared resist composition was evaluated as ○ when the thin film formability was good, and x when the formed film had defects.

(3) Pattern Evaluation of Resist Pattern

A clean silicon wafer was spin coated with the homogenous resist composition, and then prebaked (PB) before exposure in an oven of 110° C. to form a resist film with a thickness of 60 nm. The obtained resist film was irradiated with electron beams of 1:1 line and space setting with a 50 nm interval, a 40 nm interval, and a 30 nm interval using an electron beam lithography system (ELS-7500 manufactured by ELIONIX INC.). After irradiation, the resist film was heated at each predetermined temperature for 90 seconds, and immersed in 2.38% by mass TMAH alkaline developing solution for 60 seconds for development. Subsequently, the resist film was washed with ultrapure water for 30 seconds, and dried to form a positive type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

Synthesis Example

Synthesis Example 1

Synthesis of A-1 (Xanthene Compound)

In a container (internal capacity: 300 mL) equipped with a stirrer, a condenser tube, and a burette, 7.0 g (40 mmol) of 2,6-naphthalenediol (a reagent manufactured by Sigma-Aldrich) and 4.6 g (20 mmol) of 3-iodobenzaldehyde (a reagent manufactured by Tokyo Kasei Kogyo Co., Ltd.) were fed to 100 mL of γ-butyrolactone, 0.5 g of p-toluenesulfonic acid was added, and the contents were reacted by being stirred at 90° C. for 23 hours to obtain a reaction solution. Next, 1000 g of pure water was added to the reaction solution, then extracted by ethyl acetate, and concentrated to obtain a solution.

The obtained solution was separated by column chromatography and then washed with chloroform to obtain 4.2 g of the objective compound (A-1) represented by the following formula (A-1). As a result of measuring the molecular weight of the obtained compound (A-1) by the above method, it was 516.

The following peaks were found by NMR measurement performed on the obtained compound (A-1) under the above measurement conditions, and the compound was confirmed to have a chemical structure of the following formula (A-1).

δ (ppm) 9.7 (2H, O—H), 7.0-8.5 (14H, Ph-H), 6.5 (1H, C—H)

That the substituted position of 2,6-naphthalenediol was 1-position in the obtained compound (A-1) was confirmed from the signals of the protons at 3-position and 4-position being doublet.

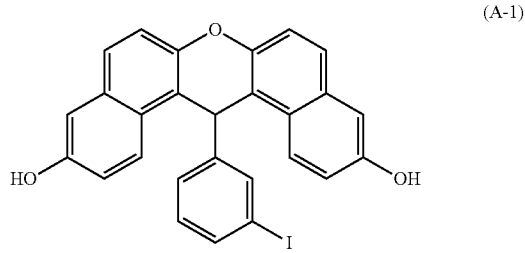 [SMILES: Oc1ccc2c3c(ccc2c1)Oc1ccc2cc(O)ccc2c1C3c1cccc(I)c1]

(A-1)

Synthesis Examples

Synthesis Example 1

Synthesis of A-1-BOC

In a container (internal capacity: 200 mL) equipped with a stirrer, a condenser tube, and a burette, 6.5 g (12.5 mmol) of the compound obtained above (A-1) and 5.5 g (25 mmol) of di-t-butyl dicarbonate (manufactured by Aldrich) were fed to 100 mL of acetone, 3.45 g (25 mmol) of potassium carbonate (manufactured by Aldrich) was added, and the contents were reacted by being stirred at 20° C. for 6 hours to obtain a reaction solution. Next, the reaction solution was concentrated. The reaction product was precipitated by the addition of 100 g of pure water to the concentrated solution. After cooling to room temperature, solid matter was separated by filtration.

The obtained solid matter was subjected to filtration, dried, and then separated and purified by column chromatography to obtain 2 g of the objective compound (A-1-BOC) represented by the following formula (A-1-BOC).

As a result of measuring the molecular weight of the obtained compound (A-1-BOC) by the above method, it was 716.

The following peaks were found by NMR measurement performed on the obtained compound (A-1-BOC) under the above measurement conditions, and the compound was confirmed to have a chemical structure of the following formula (A-1-BOC).

δ (ppm) 7.2-8.7 (14H, Ph-H), 6.8 (1H, C—H), 1.6 (18H, C—C$\underline{H}_3$)

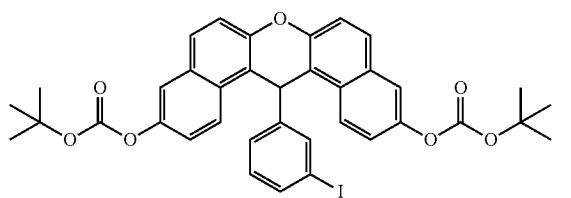

(A-1-BOC)

The solubilities of the obtained compound (A-1-BOC) in safe solvents were evaluated by the above method. The results are shown in Table 1 (Example 1).

Synthesis Example 2

Synthesis of A-1-MeBOC

In a container (internal capacity: 200 mL) equipped with a stirrer, a condenser tube, and a burette, 6.4 g (12.4 mmol) of the compound obtained above (A-1) and 5.4 g (27 mmol) of t-butyl bromoacetate (manufactured by Aldrich) were fed to 100 mL of acetone, 3.8 g (27 mmol) of potassium carbonate (manufactured by Aldrich) and 0.8 g of 18-crown-6 were added, and the contents were reacted by being stirred under reflux for 3 hours to obtain a reaction solution. Next, the reaction solution was concentrated. The reaction product was precipitated by the addition of 100 g of pure water to the concentrated solution. After cooling to room temperature, solid matter was separated by filtration.

The obtained solid matter was subjected to filtration, dried, and then separated and purified by column chromatography to obtain 1.8 g of the objective compound (A-1-MeBOC) represented by the following formula (A-1-Me-BOC).

As a result of measuring the molecular weight of the obtained compound (A-1-MeBOC) by the above method, it was 694.

The following peaks were found by NMR measurement performed on the obtained compound (A-1-MeBOC) under the above measurement conditions, and the compound was confirmed to have a chemical structure of the following formula (A-1-MeBOC).

δ (ppm) 7.2-8.7 (14H, Ph-H), 6.7 (1H, C—H), 4.7-4.8 (4H, C—C$\underline{H}_2$—C), 1.3-1.4 (18H, C—C$\underline{H}_3$)

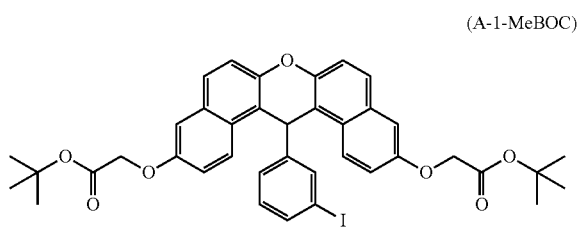 [SMILES: CC(C)(C)OC(=O)COc1ccc2c3c(ccc2c1)Oc1ccc2cc(OCC(=O)OC(C)(C)C)ccc2c1C3c1cccc(I)c1]

(A-1-MeBOC)

The solubilities of the obtained compound (A-1-MeBOC) in safe solvents were evaluated by the above method. The results are shown in Table 1 (Example 2).

Synthesis Example 2

Synthesis of A-3 (Xanthene Compound)

In a container (internal capacity: 300 mL) equipped with a stirrer, a condenser tube, and a burette, 7.0 g (40 mmol) of 2,6-naphthalenediol (a reagent manufactured by Sigma-Aldrich) and 5.6 g (20 mmol) of 5-iodovanillin (a reagent manufactured by Tokyo Kasei Kogyo Co., Ltd.) were fed to 100 mL of γ-butyrolactone, 0.5 g of p-toluenesulfonic acid was added, and the contents were reacted by being stirred at 90° C. for 87 hours to obtain a reaction solution. Next, 1000 g of pure water was added to the reaction solution, then extracted by ethyl acetate, and concentrated to obtain a solution.

The obtained solution was separated by column chromatography and then washed with chloroform to obtain 2.0 g of the objective compound (A-3) represented by the following formula (A-3). As a result of measuring the molecular weight of the obtained compound (A-3) by the above method, it was 562.

The following peaks were found by NMR measurement performed on the obtained compound (A-3) under the above measurement conditions, and the compound was confirmed to have a chemical structure of the following formula (A-3).

δ (ppm) 9.7, 9.3 (3H, O—H), 7.2-8.5 (12H, Ph-H), 6.4 (1H, C—H), 3.7 (3H, O—C—H)

That the substituted position of 2,6-naphthalenediol was 1-position in the obtained compound (A-3) was confirmed from the signals of the protons at 3-position and 4-position being doublet.

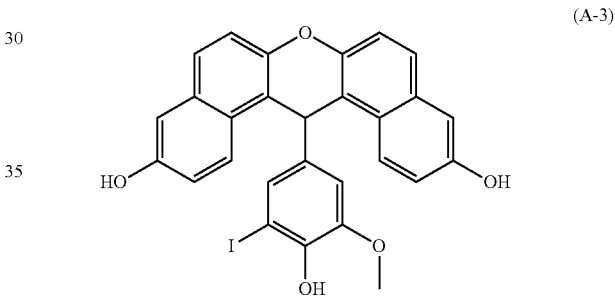

(A-3)

Synthesis Example 3

Synthesis of A-3-BOC

In a container (internal capacity: 200 mL) equipped with a stirrer, a condenser tube, and a burette, 7.0 g (12.5 mmol) of the compound obtained above (A-3) and 8.2 g (37.5 mmol) of di-t-butyl dicarbonate (manufactured by Aldrich) were fed to 100 mL of acetone, 5.2 g (37.5 mmol) of potassium carbonate (manufactured by Aldrich) was added, and the contents were reacted by being stirred at 20° C. for 6 hours to obtain a reaction solution. Next, the reaction solution was concentrated. The reaction product was precipitated by the addition of 100 g of pure water to the concentrated solution. After cooling to room temperature, solid matter was separated by filtration.

The obtained solid matter was subjected to filtration, dried, and then separated and purified by column chromatography to obtain 1.6 g of the objective compound (A-3-BOC) represented by the following formula (A-3-BOC). As a result of measuring the molecular weight of the obtained compound (A-3-BOC) by the above method, it was 862.

The following peaks were found by NMR measurement performed on the obtained compound (A-3-BOC) under the above measurement conditions, and the compound was confirmed to have a chemical structure of the following formula (A-3-BOC).

δ (ppm) 7.4-8.7 (12H, Ph-H), 6.4 (1H, C—H), 3.8 (3H, O—C—H), 1.6 (27H, C—C$\underline{H}_3$)

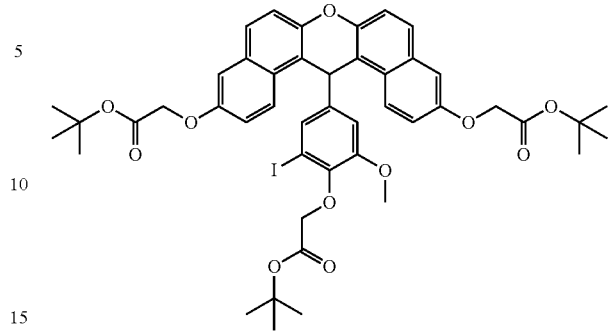

(A-3-MeBOC)

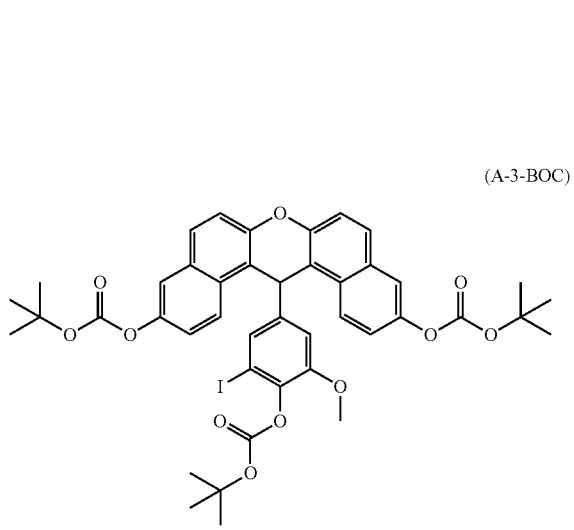 [SMILES: COc1cc(C2c3c(ccc4cc(OC(=O)OC(C)(C)C)ccc34)Oc3ccc4cc(OC(=O)OC(C)(C)C)ccc4c32)cc(I)c1OC(=O)OC(C)(C)C]

(A-3-BOC)

The solubilities of the obtained compound (A-3-BOC) in safe solvents were evaluated by the above method. The results are shown in Table 1 (Example 3).

The solubilities of the obtained compound (A-3-MeBOC) in safe solvents were evaluated by the above method. The results are shown in Table 1 (Example 4).

Synthesis Example 3

Synthesis of B-1 (Xanthene Compound)

The same operations as in Synthesis Example 1 were performed except that 7.0 g (40 mmol) of 2,7-naphthalenediol (a reagent manufactured by Sigma-Aldrich) was used in place of 7.0 g (40 mmol) of 2,6-naphthalenediol, to obtain 4.0 g of the objective compound (B-1) having a structure represented by the following formula (B-1).

As a result of measuring the molecular weight of the obtained compound (B-1) by the above method, it was 516.

The following peaks were found by NMR measurement performed on the obtained compound (B-1) under the above measurement conditions, and the compound was confirmed to have a chemical structure of the following formula (B-1).

δ (ppm) 9.9 (2H, O—H), 7.0-7.8 (14H, Ph-H), 6.1 (1H, C—H)

That the substituted position of 2,7-naphthalenediol was 1-position in the obtained compound (B-1) was confirmed from the signals of the protons at 3-position and 4-position being doublet.

Synthesis Example 4

Synthesis of A-3-MeBOC

In a container (internal capacity: 200 mL) equipped with a stirrer, a condenser tube, and a burette, 7.0 g (12.4 mmol) of the compound obtained above (A-3) and 7.9 g (40.5 mmol) of t-butyl bromoacetate (manufactured by Aldrich) were fed to 100 mL of acetone, 5.6 g (40.5 mmol) of potassium carbonate (manufactured by Aldrich) and 1.2 g of 18-crown-6 were added, and the contents were reacted by being stirred under reflux for 3 hours to obtain a reaction solution. Next, the reaction solution was concentrated. The reaction product was precipitated by the addition of 100 g of pure water to the concentrated solution. After cooling to room temperature, solid matter was separated by filtration.

The obtained solid matter was subjected to filtration, dried, and then separated and purified by column chromatography to obtain 1.8 g of the objective compound (A-3-MeBOC) represented by the following formula (A-3-MeBOC).

As a result of measuring the molecular weight of the obtained compound (A-3-MeBOC) by the above method, it was 904.

The following peaks were found by NMR measurement performed on the obtained compound (A-3-MeBOC) under the above measurement conditions, and the compound was confirmed to have a chemical structure of the following formula (A-3-MeBOC).

δ (ppm) 7.4-8.7 (12, Ph-H), 6.3 (1H, C—H), 4.7-4.8 (6H, C—C$\underline{H}_2$—C), 3.7 (3H, O—C—H), 1.3-1.4 (27H, C—C$\underline{H}_3$)

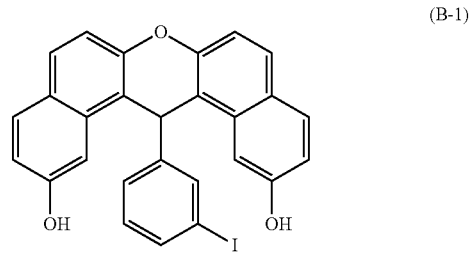 [SMILES: Oc1ccc2ccc3c(c2c1)C(c1cccc(I)c1)c1c(ccc2ccc(O)cc12)O3]

(B-1)

Synthesis Example 5

Synthesis of B-1-BOC

The same operations as in Synthesis Example 1 were performed except that 6.5 g (12.5 mmol) of the compound (B-1) was used in place of 6.5 g (12.5 mmol) of the compound (A-1), to obtain 2.0 g of the objective compound (B-1-BOC) having a structure represented by the following formula (B-1-BOC).

As a result of measuring the molecular weight of the obtained compound (B-1-BOC) by the above method, it was 716.

The following peaks were found by NMR measurement performed on the obtained compound (B-1-BOC) under the above measurement conditions, and the compound was confirmed to have a chemical structure of the following formula (B-1-BOC).

δ (ppm) 7.2-8.0 (14H, Ph-H), 6.4 (1H, C—H), 1.6 (18H, C—C$\underline{H}_3$)

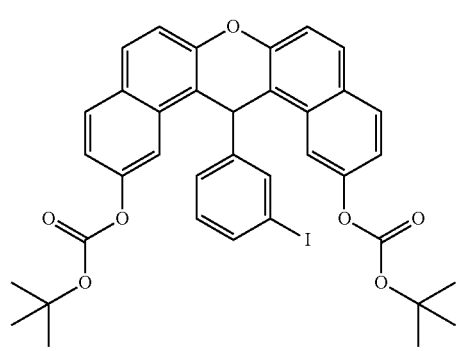

(B-1-BOC)

The solubilities of the obtained compound (A-1-BOC) in safe solvents were evaluated by the above method. The results are shown in Table 1 (Example 5).

Synthesis Example 6

Synthesis of B-1-MeBOC

The same operations as in Synthesis Example 2 were performed except that 6.4 g (12.4 mmol) of the compound (B-1) was used in place of 6.4 g (12.4 mmol) of the compound (A-1), to obtain 1.6 g of the objective compound (B-1-MeBOC) having a structure represented by the following formula (B-1-MeBOC).

As a result of measuring the molecular weight of the obtained compound (B-1-MeBOC) by the above method, it was 694.

The following peaks were found by NMR measurement performed on the obtained compound (B-1-MeBOC) under the above measurement conditions, and the compound was confirmed to have a chemical structure of the following formula (B-1-MeBOC).

δ (ppm) 7.2-8.0 (14H, Ph-H), 6.3 (1H, C—H), 4.7-4.8 (4H, C—C$\underline{H}_2$—C), 1.3-1.4 (18H, C—C$\underline{H}_3$)

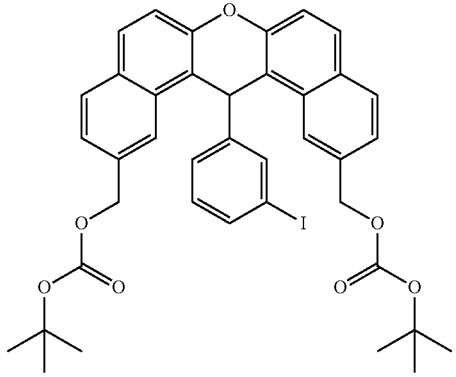

(B-1-MeBOC)

The solubilities of the obtained compound (B-1-MeBOC) in safe solvents were evaluated by the above method. The results are shown in Table 1 (Example 6).

Synthesis Example 4

Synthesis of R1A-1

To a container (internal capacity: 100 ml) equipped with a stirrer, a condenser tube, and a burette, 10.8 g (21 mmol) of the compound (A-1), 0.7 g (42 mmol) of paraformaldehyde, 50 ml of glacial acetic acid, and 50 ml of PGME were fed, 8 ml of 95% sulfuric acid was added, and the reaction solution was stirred at 100° C. for 6 hours and reacted. Next, the reaction solution was concentrated. The reaction product was precipitated by the addition of 1000 ml of methanol. After cooling to room temperature, the precipitates were separated by filtration. The obtained solid matter was subjected to filtration, dried, and then separated and purified by column chromatography to obtain 7.2 g of the objective resin (R1A-1) having a structure represented by the following formula (R1A-1).

As a result of measuring the molecular weight in terms of polystyrene of the obtained resin (R1A-1) by the above method, it was Mn: 831, Mw: 1846, Mw/Mn: 2.22.

The following peaks were found by NMR measurement performed on the obtained resin (R1A-1) under the above measurement conditions, and the resin was confirmed to have a chemical structure of the following formula (R1A-1).

δ (ppm) 9.7 (2H, O—H), 7.0-8.5 (12H, Ph-H), 6.5 (1H, C—H), 4.1 (2H, —CH$_2$)

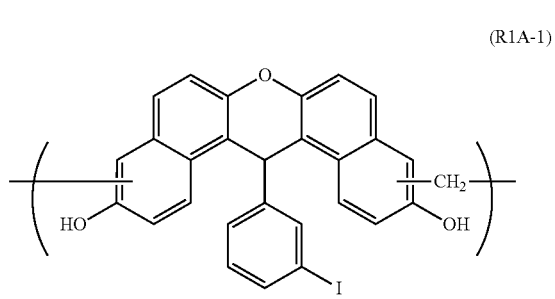

(R1A-1)

Synthesis Example 7

Synthesis of R1A-1-BOC

The same operations as in Synthesis Example 1 were performed except that 23.1 g of the resin (R1A-1) was used in place of 6.5 g (12.5 mmol) of the compound (A-1), to obtain 7.5 g of the objective resin (R1A-1-BOC) having a structure represented by the following formula (R1A-1-BOC).

As a result of measuring the molecular weight in terms of polystyrene of the obtained resin (R1A-1-BOC) by the above method, it was Mn: 1031, Mw: 2299, Mw/Mn: 2.23.

The following peaks were found by NMR measurement performed on the obtained resin (R1A-1-BOC) under the above measurement conditions, and the resin was confirmed to have a chemical structure of the following formula (R1A-1-BOC).

δ (ppm) 7.2-8.7 (14H, Ph-H), 6.8 (1H, C—H), 1.6 (18H, C—C$\underline{H}_3$)

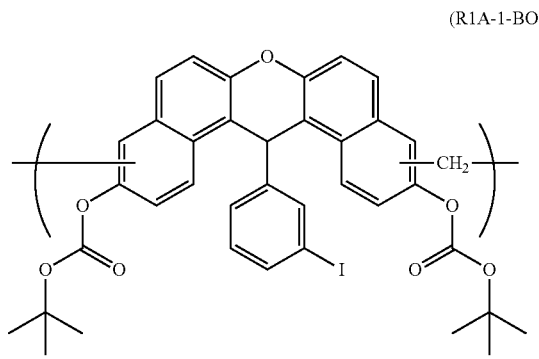

(R1A-1-BOC)

The solubilities of the obtained resin (R1A-1-BOC) in safe solvents were evaluated by the above method. The results are shown in Table 1 (Example 7).

Synthesis Example 5

Synthesis of R2A-1

The same operations as in Synthesis Example 4 were performed except that 7.6 g (42 mmol) of 4-biphenylcarboxyaldehyde (manufactured by Mitsubishi Gas Chemical Company Inc.) was used in place of 0.7 g (42 mmol) of paraformaldehyde, to obtain 7.6 g of the objective resin (R2A-1) having a structure represented by the following formula (R2A-1).

As a result of measuring the molecular weight in terms of polystyrene of the obtained resin (R2A-1) by the above method, it was Mn: 614, Mw: 1338, Mw/Mn: 2.18.

The following peaks were found by NMR measurement performed on the obtained resin (R2A-1) under the above measurement conditions, and the resin was confirmed to have a chemical structure of the following formula (R2A-1).

δ (ppm) 9.7 (2H, O—H), 7.0-8.8 (21H, Ph-H), 6.6 (1H, C—H), 4.5 (1H, —CH)

Moreover, the solubilities of the obtained resin (R2A-1) in safe solvents were evaluated by the above method. The results are shown in Table 1.

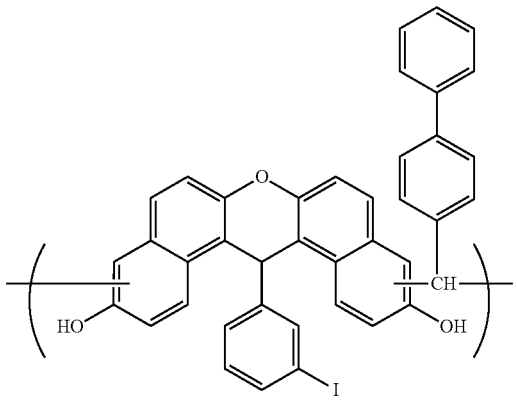

(R2A-1)

Synthesis Example 8

Synthesis of R2A-1-BOC

The same operations as in Synthesis Example 1 were performed except that 16.8 g of the resin (R2A-1) was used in place of 6.5 g (12.5 mmol) of the compound (A-1), to obtain 5.0 g of the objective resin (R1A-1-BOC) having a structure represented by the following formula (R1A-1-BOC).

As a result of measuring the molecular weight in terms of polystyrene of the obtained resin (R1A-1-BOC) by the above method, it was Mn: 910, Mw: 2002, Mw/Mn: 2.20.

The following peaks were found by NMR measurement performed on the obtained resin (R1A-1-BOC) under the above measurement conditions, and the resin was confirmed to have a chemical structure of the following formula (R1A-1-BOC).

δ (ppm) 7.2-9.0 (21H, Ph-H), 6.9 (1H, C—H), 4.6 (1H, —CH), 1.6 (18H, C—C$\underline{H}_3$)

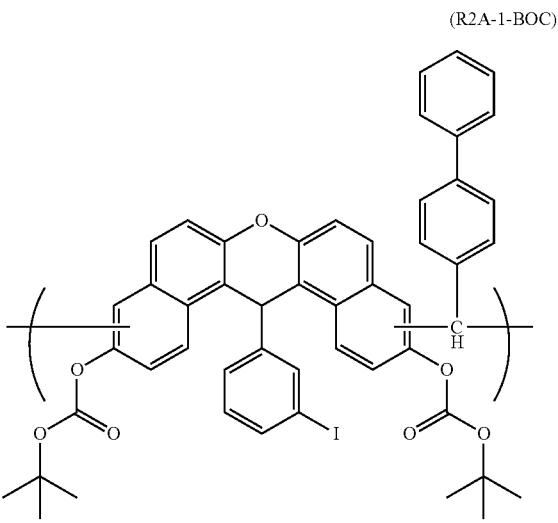

(R2A-1-BOC)

The solubilities of the obtained resin (R1A-1-BOC) in safe solvents were evaluated by the above method. The results are shown in Table 1 (Example 8).

Comparative Synthesis Example 1

Synthesis of XBisN-1

In a container (internal capacity: 100 mL) equipped with a stirrer, a condenser tube, and a burette, 3.20 g (20 mmol) of 2,6-naphthalenediol (a reagent manufactured by Sigma-Aldrich) and 1.82 g (10 mmol) of 4-biphenylcarboxyaldehyde (manufactured by Mitsubishi Gas Chemical Company Inc.) were fed to 30 mL of methyl isobutyl ketone, 5 mL of 95% sulfuric acid was added, and the contents were reacted by being stirred at 30° C. for 6 hours to obtain a reaction solution. Next, the reaction solution was concentrated. The reaction product was precipitated by the addition of 50 g of pure water to the concentrated solution. After cooling to room temperature, solid matter was separated by filtration.

The obtained solid matter was subjected to filtration, dried, and then separated and purified by column chromatography to obtain 0.2 g of the objective compound (XBisN-1) represented by the following formula (XBisN-1).

As a result of measuring the molecular weight of the obtained compound (XBisN-1) by the above method, it was 466.

The following peaks were found by NMR measurement performed on the obtained compound (XBisN-1) under the above measurement conditions, and the compound was confirmed to have a chemical structure of the following formula (XBisN-1).

δ (ppm) 9.3-9.4 (4H, O—H), 7.0-8.5 (19H, Ph-H), 6.8 (1H, C—H)

That the substituted position of 2,6-naphthalenediol was 1-position in the obtained compound (XBisN-1) was confirmed from the signals of the protons at 3-position and 4-position being doublet.

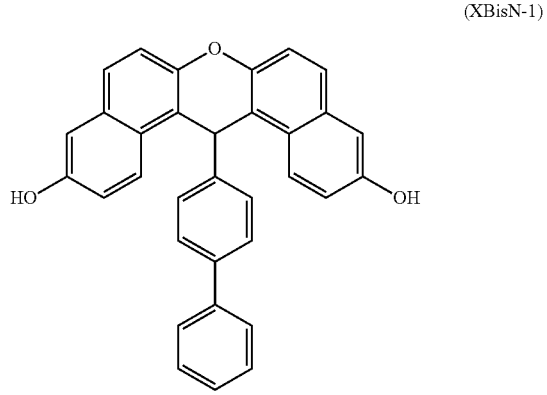 [SMILES: Oc1ccc2c3c(ccc2c1)Oc1ccc2cc(O)ccc2c1C3c1ccc(-c2ccccc2)cc1]

(XBisN-1)

Synthesis of XBisN-1-BOC

In a container (internal capacity: 200 mL) equipped with a stirrer, a condenser tube, and a burette, 5.8 g (12.5 mmol) of the compound obtained above (XBisN-1) and 5.5 g (25 mmol) of di-t-butyl dicarbonate (manufactured by Aldrich) were fed to 100 mL of acetone, 3.45 g (25 mmol) of potassium carbonate (manufactured by Aldrich) was added, and the contents were reacted by being stirred at 20° C. for 6 hours to obtain a reaction solution. Next, the reaction solution was concentrated. The reaction product was precipitated by the addition of 100 g of pure water to the concentrated solution. After cooling to room temperature, solid matter was separated by filtration.

The obtained solid matter was subjected to filtration, dried, and then separated and purified by column chromatography to obtain 2 g of the objective compound (XBisN-1-BOC) represented by the following formula (XBisN-1-BOC).

As a result of measuring the molecular weight of the obtained compound (XBisN-1-BOC) by the above method, it was 666.

The following peaks were found by NMR measurement performed on the obtained compound (XBisN-1-BOC) under the above measurement conditions, and the compound was confirmed to have a chemical structure of the following formula (XBisN-1-BOC).

δ (ppm) 7.2-8.7 (19H, Ph-H), 6.8 (1H, C—H), 1.6 (18H, C—C$\underline{H}_3$)

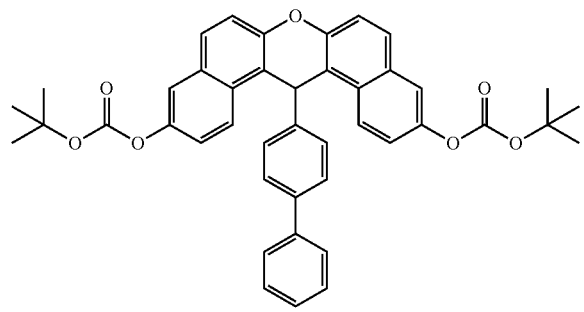

(XBisN-1-BOC)

The solubilities of the obtained compound (XBisN-1-BOC) in safe solvents were evaluated by the above method. The results are shown in Table 1 (Comparative Example 1).

Comparative Synthesis Example 2

Synthesis of CR-1 (Polyphenol Compound)

74.3 g (3.71 mol) of anhydrous HF and 50.5 g (0.744 mol) of $BF_3$ were fed to a temperature-controllable autoclave (made of SUS 316L) having an internal capacity of 500 mL and equipped with an electromagnetic stirrer, and the contents were stirred and increased in pressure with carbon monoxide to 2 MPa while maintaining the liquid temperature at −30° C. Thereafter, while maintaining the autoclave at a pressure of 2 MPa and a fluid temperature of −30° C., a raw material mixture of 57.0 g (0.248 mol) of 4-cyclohexylbenzene and 50.0 g of n-heptane was fed and retained for 1 hour, and then the contents were collected into ice. The collected contents were diluted with benzene and neutralized to obtain an oil layer. The obtained oil layer was analyzed by gas chromatography to determine the outcome of the reaction. The 4-cyclohexylbenzene conversion was 100%, and the 4-cyclohexylbenzaldehyde selectivity was 97.3%.

The objective component was isolated from the obtained oil layer by simple distillation and analyzed by GC-MS, thus showing that the molecular weight of 4-cyclohexylbenzaldehyde (CHBAL) of the following formula (CHBAL) was 188. The obtained compound (CHBAL) was subjected to NMR measurement under the above measurement conditions and thus confirmed as having the chemical structure of the following formula (CHBAL).

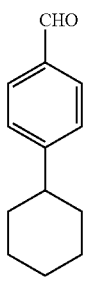

(CHBAL)

Under a nitrogen gas stream, resorcinol (22 g, 0.2 mol) manufactured by Kanto Chemical Co., Inc., the compound obtained above (CHBAL) (46.0 g, 0.2 mol), and dehydrated ethanol (200 mL) were introduced into a four necked flask (1000 mL) that had been sufficiently dried, substituted with nitrogen, and equipped with a dropping funnel, a Dimroth condenser tube, a thermometer, and a stirring blade, to prepare an ethanol solution. This solution was heated to 85° C. by a mantle heater while stirring. Then, 75 mL of concentrated hydrochloric acid (35%) was added dropwise through the dropping funnel over 30 minutes to the solution, and continuously the solution was stirred at 85° C. for 3 hours to allow the reaction to proceed. After the reaction terminated, the obtained reaction solution was stood to cool, and after reaching room temperature, the reaction solution was cooled in an ice bath. The reaction solution was left to stand still for 1 hour, producing the objective light yellow crude crystals, which were filtered. The filtered crude crystals were washed twice with 500 mL of methanol, filtered, and dried in a vacuum to obtain 50 g of the product (CR-1) represented by the following formula (CR-1).

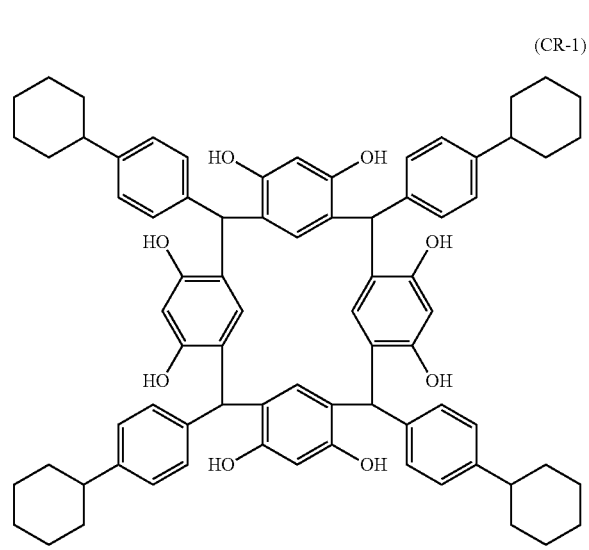 [SMILES: Oc1cc(O)c2cc1C(c1ccc(C3CCCCC3)cc1)c1cc(c(O)cc1O)C(c1ccc(C3CCCCC3)cc1)c1cc(c(O)cc1O)C(c1ccc(C3CCCCC3)cc1)c1cc(c(O)cc1O)C2c1ccc(C2CCCCC2)cc1]

(CR-1)

Synthesis of CR-1-BOC

Subsequently, CR-1 and di-t-butyl dicarbonate were reacted in the same manner as in Synthesis Example 1 to obtain 25 g of the objective compounds (CR-1-BOC) represented by the following formula (CR-1-BOC).

The obtained compound (CR-1-BOC) was subjected to NMR measurement under the above measurement conditions and confirmed as having the chemical structure of the following formula (CR-1-BOC).

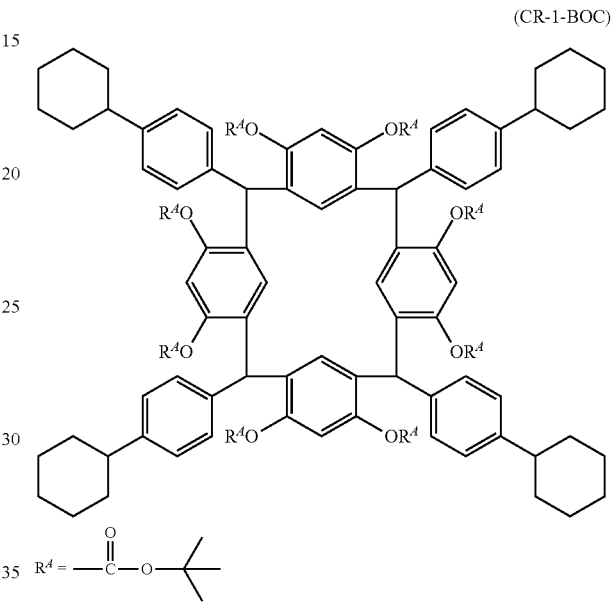

(CR-1-BOC)

The solubilities of the obtained compound (CR-1-BOC) in safe solvents were evaluated by the above method. The results are shown in Table 1 (Comparative Example 2).

Examples 1 to 8 and Comparative Examples 1 to 2

Synthesis of Resist Composition

Using the compounds each synthesized above, resin compositions were prepared according to the formulations shown in Table 1. Of the components of the resist compositions in Table 1, the acid generating agent (C), the acid diffusion controlling agent (E), and the solvent used were as follows.

Acid Generating Agent (C)

P-1: triphenylbenzenesulfonium trifluoromethanesulfonate (Midori Kagaku Co., Ltd.)

Acid Diffusion Controlling Agent (E)

Q-1: trioctylamine (Tokyo Kasei Kogyo Co., Ltd.)

Solvent

S-1: propylene glycol monomethyl ether (Tokyo Kasei Kogyo Co., Ltd.)

The storage stabilities of the obtained resist compositions were evaluated by the above method. Thin film formability was evaluated using the resist compositions in a homogenous state. The obtained results are shown in Table 1.

TABLE 1

| | | Safe solvent | | | Resist performance evaluation Resist composition | | | | | |
|---|---|---|---|---|---|---|---|---|---|---|
| | Polyphenol derivative | CHN | PGME | PGMEA | Compound of Synthetic Example [g] | Acid generating agent (C) P-1 [g] | Acid diffusion controlling agent (E) Q-1 [g] | Solvent S-1 [g] | Stability evaluation | Thin film formability |
| Example 1 | A-1-BOC | A | A | A | 1.0 | 0.3 | 0.03 | 50.0 | ○ | ○ |
| Example 2 | A-1-MeBOC | A | A | A | 1.0 | 0.3 | 0.03 | 50.0 | ○ | ○ |
| Example 3 | A-3-BOC | A | A | B | 1.0 | 0.3 | 0.03 | 50.0 | ○ | ○ |
| Example 4 | A-3-MeBOC | A | A | A | 1.0 | 0.3 | 0.03 | 50.0 | ○ | ○ |
| Example 5 | B-1-BOC | A | A | A | 1.0 | 0.3 | 0.03 | 50.0 | ○ | ○ |
| Example 6 | B-1-MeBOC | A | A | A | 1.0 | 0.3 | 0.03 | 50.0 | ○ | ○ |
| Example 7 | R1A-1-BOC | A | A | A | 1.0 | 0.3 | 0.03 | 50.0 | ○ | ○ |
| Example 8 | R2A-1-BOC | A | A | A | 1.0 | 0.3 | 0.03 | 50.0 | ○ | ○ |
| Comparative Example 1 | XBisN-1-BOC | A | B | A | 1.0 | 0.3 | 0.03 | 50.0 | X | ○ |
| Comparative Example 2 | CR-1-BOC | B | B | C | 1.0 | 0.3 | 0.03 | 50.0 | X | X |

As can be understood from Table 1, it was able to be confirmed that the compounds used in Examples 1 to 8 and Comparative Example 1 (A-1-BOC, A-1-MeBOC, A-3-BOC, A-3-MeBOC, B-1-BOC, B-1-MeBOC, R1A-1-BOC, R2A-1-BOC, and XBisN-1-BOC in this order) had good solubility, but the compound (CR-1-BOC) used in Comparative Example 2 had inferior solubility.

The resist compositions obtained in Examples 1 to 8 did not yield precipitates and were confirmed as having good storage stability (evaluation: ○). On the other hand, the resist compositions obtained in Comparative Examples 1 and 2 yielded precipitates and were confirmed as having poor storage stability (evaluation: x).

Moreover, the resist compositions obtained in Examples 1 to 8 and Comparative Example 1 were confirmed as having good thin film formability (evaluation: ○). On the other hand, the resist composition obtained in Comparative Example 2 resulted in film defects and was confirmed as having poor thin film formability (evaluation: x).

Pattern evaluation was carried out according to the above method using the resist compositions obtained in Examples 1 and 2. Good resist patterns were obtained by irradiation with electron beams of 1:1 line and space setting with a 50 nm interval.

From the above results, it was found that the compounds meeting the requirements of the present invention have high solubility in safe solvents, and resist compositions containing the compounds have good storage stability and can impart a shape to a resist pattern compared with resist compositions containing comparative compounds (XBisN-1-BOC) and (CR-1-BOC). As long as the above requirements of the present invention are met, compounds other than the compounds described in examples also exhibit the same effects.

Examples

Production of PGMEA Solution of Compound Represented by Above General Formula (4) Having Reduced Metal Content Example 9

To a 4-neck flask (bottom-less type) having a volume of 1000 mL, 150 g of a solution (2.5% by mass) containing A-1-BOC dissolved in PGMEA was fed, and heated to 80° C. while being stirred. Next, 37.5 g of an aqueous oxalic acid solution (pH 1.3) was added, and the mixture was stirred for 5 minutes and then left to stand still for 30 minutes. Accordingly, the mixture was separated into an oil phase and an aqueous phase, and the aqueous phase was removed. After this operation was repeated once, 37.5 g of ultrapure water was fed to the obtained oil phase, and the mixture was stirred for 5 minutes and then left to stand still for 30 minutes to remove the aqueous phase. By repeating this operation 3 times, a PGMEA solution of A-1-BOC having a reduced metal content was obtained.

Example 10

A PGMEA solution of A-1-BOC was obtained in the same manner as in Example 9 except that 135 g of PGMEA (120 g)/PGME (15 g) (10% by mass) was fed in place of 150 g of PGMEA (2.5% by mass).

Example 11

A PGMEA solution of A-1-BOC was obtained in the same manner as in Example 10 except that 130 g of an aqueous citric acid solution (pH 1.8) was fed in place of 37.5 g of an aqueous oxalic acid solution (pH 1.3).

Reference Example 1

Production of Compound Having Reduced Metal Content with Ion Exchange Resin

After 25 g of an ion exchange resin (Mitsubishi Chemical Corporation Diaion: SMT100-mixed resin) was swollen by cyclohexanone, a Teflon (R) column was filled with the ion exchange resin, and 500 mL of 1,3-dioxolane was passed through for solvent displacement. Next, 500 g of a solution (1.7% by mass) containing A-1-BOC dissolved in 1,3-dioxolane was passed through to obtain a dioxolane solution of A-1-BOC.

The contents of various metals in the 10% by mass PGMEA solution of A-1-BOC that was before treatment and in the solutions of the compound represented by formula (1)

or formula (2) obtained in Examples 9 to 11 and Reference Example 1 were measured by ICP-MS. The measurement results are shown in Table 2.

TABLE 2

|  | Metal content (ppb) | | | | | |
| --- | --- | --- | --- | --- | --- | --- |
|  | Na | Mg | K | Fe | Cu | Zn |
| A-1-BOC before treatment | 37 | 1.3 | 1.4 | >99 | 3.1 | 12.4 |
| Example 9 | ≤0.2 | ≤0.2 | ≤0.2 | ≤0.2 | ≤0.2 | ≤0.2 |
| Example 10 | ≤0.2 | ≤0.2 | ≤0.2 | ≤0.2 | ≤0.2 | ≤0.2 |
| Example 11 | ≤0.2 | ≤0.2 | ≤0.2 | ≤0.2 | ≤0.2 | ≤0.2 |
| Reference Example 1 | ≤0.2 | 0.3 | 1.0 | >99 | 1.5 | 0.9 |

INDUSTRIAL APPLICABILITY

The resist composition of the present invention contains a compound that has a specific structure and high solubility in a safe solvent, has good storage stability, is capable of forming a thin film, and can impart a good shape to a resist pattern. Accordingly, the present invention is useful in the semiconductor field, the display field, photomasks, thin film magnetic heads, compound semiconductors, research and development, and the like where resist compositions such as acid-amplified non-polymeric resist materials are used.

Moreover, according to the present invention, it is possible to provide a compound (such as a polyphenol derivative) that has high solubility in a safe solvent and good storage stability and is capable of forming a thin film. Accordingly, the present invention is suitably used for a base material of photosensitive materials such as photoresists for semiconductors, a raw material or a curing agent of an epoxy resin used for, for example, encapsulating materials of integrated circuits, a color developer or a discoloration inhibitor used for heat-sensitive recording materials, and, in addition, an additive for germicides and antimicrobial/antifungal agents, etc.

Moreover, the present invention can produce in an industrially advantageous manner a compound represented by the above general formula (1), a compound represented by the above general formula (2), or a resin obtained using these as monomers, which have a reduced metal content.

The invention claimed is:

1. A resist composition comprising one or more selected from a compound represented by the following general formula (1), a compound represented by the following general formula (2), and a resin obtained using these as monomers:

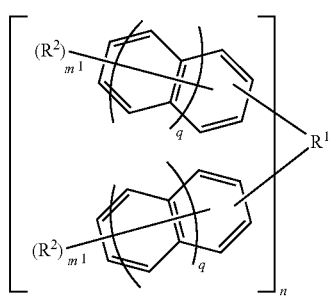

(1)

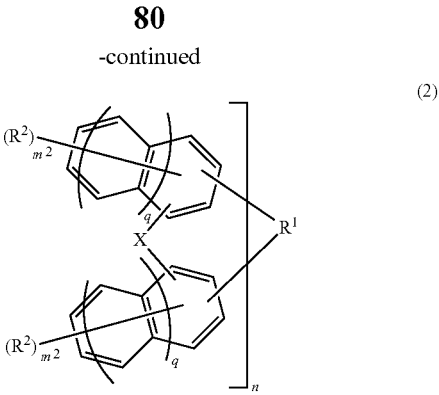

(2)

wherein $R^1$ is a 2n-valent group of 1 to 30 carbon atoms; each $R^2$ is independently a halogen atom, a linear, branched, or cyclic alkyl group of 1 to 10 carbon atoms, an aryl group of 6 to 10 carbon atoms, an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater in the general formulae (1) and (2), structural formulae of n repeating units may be the same or different; in the general formula (1), each $m^1$ is independently an integer of 0 to 7, provided that at least one $m^1$ is an integer of 1 to 7; in the general formula (2), each X is independently an oxygen atom or a sulfur atom, and each is independently an integer of 0 to 6, provided that at least one $m^2$ is an integer of 1 to 6; and in the general formulae (1) and (2), each q is independently 0 or 1; provided that in the general formulae (1) and (2), at least one $R^2$ is a group obtained by replacing a hydrogen atom of a hydroxy group with an acid dissociation group, and $R^1$ is a group comprising an iodine atom, wherein the composition further comprises a solvent, an acid generating agent, and an acid diffusion controlling agent.

2. The resist composition according to claim 1, wherein the compound represented by the above general formula (1) is a compound represented by the following general formula (1-1), and the compound represented by the above general formula (2) is a compound represented by the following general formula (2-1):

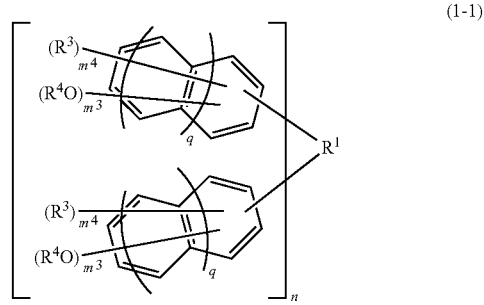

(1-1)

-continued (2-1)

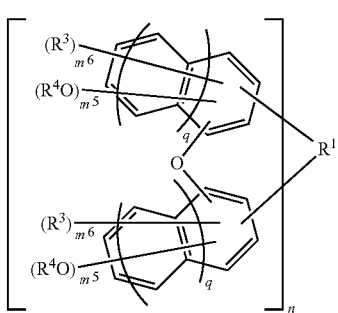

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater in the general formulae (1-1) and (2-1), structural formulae of n repeating units may be the same or different; in the general formula (1-1), each $m^3$ is independently an integer of 1 to 7, each $m^4$ is independently an integer of 0 to 6, and $m^3+m^4$ is an integer of 1 to 7; in the general formula (2-1), each $m^5$ is independently an integer of 1 to 6, each $m^6$ is independently an integer of 0 to 5, and $m^5+m^6$ is an integer of 1 to 6; and in the general formulae (1-1) and (2-1), each q is independently 0 or 1; provided that in the general formulae (1-1) and (2-1), at least one $R^4$ is an acid dissociation group, and $R^1$ is a group comprising an iodine atom.

3. The resist composition according to claim 1, wherein the compound represented by the above general formula (1) is a compound represented by the following general formula (1-2), and the compound represented by the above general formula (2) is a compound represented by the following general formula (2-2):

(1-2)

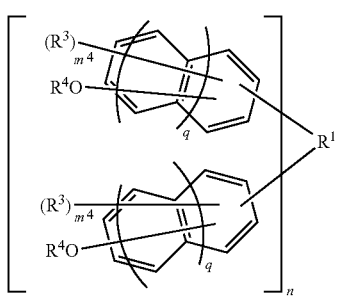

-continued (2-2)

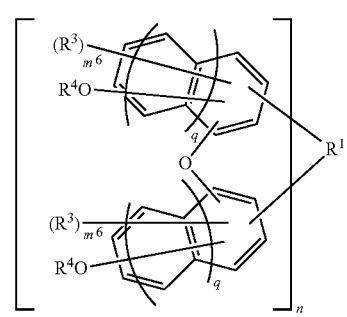

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater in the general formulae (1-2) and (2-2), structural formulae of n repeating units may be the same or different; in the general formula (1-2), each $m^4$ is independently an integer of 0 to 6; in the general formula (2-2), each $m^6$ is independently an integer of 0 to 5; and in the general formulae (1-2) and (2-2), each q is independently 0 or 1; provided that in the general formulae (1-2) and (2-2), at least one $R^4$ is an acid dissociation group, and $R^1$ is a group comprising an iodine atom.

4. A method for forming a resist pattern, comprising the steps of coating a substrate with the resist composition according to claim 1, thereby forming a resist film; exposing the formed resist film; and developing the exposed resist film.

5. The resist composition according to claim 1, wherein the compound represented by the above general formula (1) is a compound represented by the following general formula (3), and the compound represented by the above general formula (2) is a compound represented by the following general formula (4):

(3)

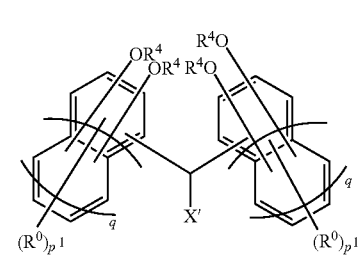

(4)

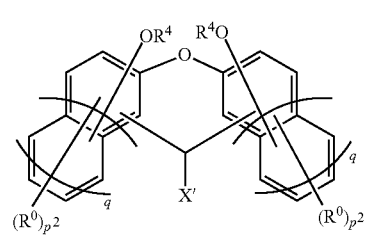

wherein X' is a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; in the general formula (3), each $p^1$ is independently an integer of 0 to 5; in the general formula (4), each $p^2$ is independently an integer of 0 to 5; and in the general formulae (3) and (4), each q is independently 0 or 1; provided that in the general formulae (3) and (4), at least one R4 is an acid dissociation group, and X' is a group comprising an iodine atom.

6. A compound represented by the following general formula (1):

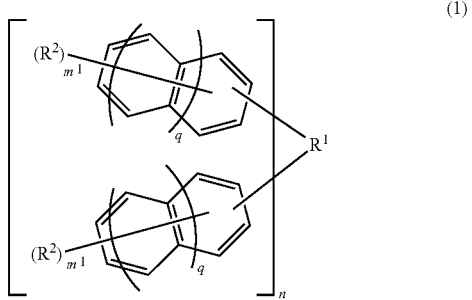

(1)

wherein $R^1$ is a 2n-valent group of 1 to 30 carbon atoms; each $R^2$ is independently a halogen atom, a linear, branched, or cyclic alkyl group of 1 to 10 carbon atoms, an aryl group of 6 to 10 carbon atoms, or an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater, structural formulae of n repeating units may be the same or different; each $m^1$ is independently an integer of 0 to 7, provided that at least one $m^1$ is an integer of 1 to 7; and each q is independently 0 or 1; provided that in the general formula (1), at least one $R^2$ is a group obtained by replacing a hydrogen atom of a hydroxy group with an acid dissociation group, and $R^1$ is a group comprising an iodine atom.

7. The compound according to claim 6, wherein the compound represented by the above general formula (1) is a compound represented by the following general formula (1-1):

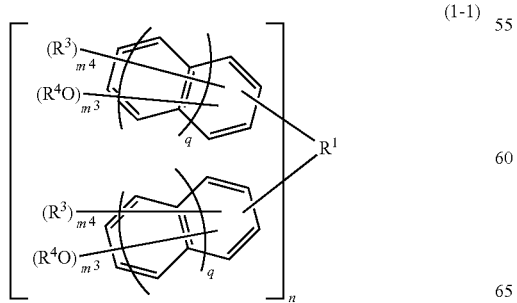

(1-1)

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^3$ is independently an integer of 1 to 7, each $m^4$ is independently an integer of 0 to 6, and $m^3+m^4$ is an integer of 1 to 7; and each q is independently 0 or 1; provided that in the general formula (1-1), at least one $R^4$ is an acid dissociation group, and $R^1$ is a group comprising an iodine atom.

8. The compound according to claim 6, wherein the compound represented by the above general formula (1) is a compound represented by the following general formula (1-2):

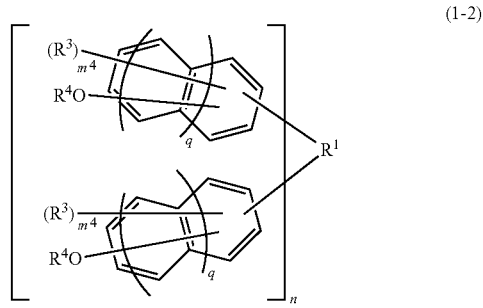

(1-2)

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^4$ is independently an integer of 0 to 6, and each q is independently 0 or 1; provided that in the general formula (1-2), at least one $R^4$ is an acid dissociation group, and $R^1$ is a group comprising an iodine atom.

9. The compound according to claim 6, wherein the compound represented by the above general formula (1) is a compound represented by the following general formula (3):

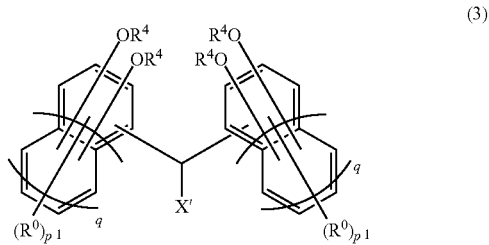

(3)

wherein X' is a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; each $p^1$ is independently an integer of 0 to 5; and each q is independently 0 or 1; provided that in the general formula (3), at least one $R^4$ is an acid dissociation group, and X' is a group comprising an iodine atom.

10. A compound represented by the following general formula (2):

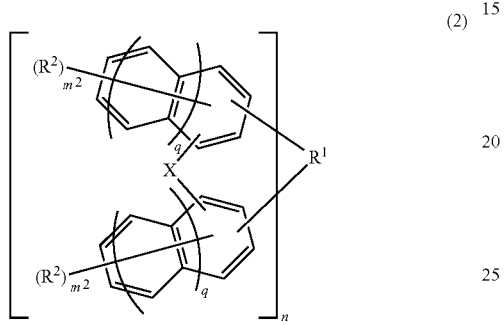

(2)

wherein $R^1$ is a 2n-valent group of 1 to 30 carbon atoms; each $R^2$ is independently a halogen atom, a linear, branched, or cyclic alkyl group of 1 to 10 carbon atoms, an aryl group of 6 to 10 carbon atoms, or an alkenyl group of 2 to 10 carbon atoms, a hydroxy group, or a group obtained by replacing a hydrogen atom of a hydroxy group with an acid dissociation group, and may be the same or different on the same naphthalene ring or benzene ring; n is an integer of 1 to 4, and when n is an integer of 2 or greater, structural formulae of n repeating units may be the same or different; each X is independently an oxygen atom or a sulfur atom; each $m^2$ is independently an integer of 0 to 6, provided that at least one $m^2$ is an integer of 1 to 6; and each q is independently 0 or 1; provided that in the general formula (2), at least one $R^2$ is a group obtained by replacing a hydrogen atom of a hydroxy group with an acid dissociation group, and $R^1$ is a group comprising an iodine atom.

11. The compound according to claim 10, wherein the compound represented by the above general formula (2) is a compound represented by the following general formula (2-1):

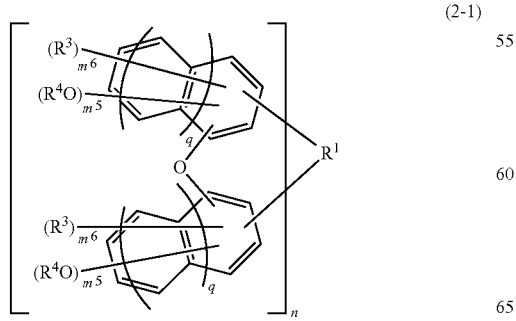

(2-1)

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^5$ is independently an integer of 1 to 6, each $m^6$ is independently an integer of 0 to 5, and $m^5+m^6$ is an integer of 1 to 6; and each q is independently 0 or 1; provided that in the general formula (2-1), at least one $R^4$ is an acid dissociation group, and $R^1$ is a group comprising an iodine atom.

12. The compound according to claim 10, wherein the compound represented by the above general formula (2) is a compound represented by the following general formula (2-2):

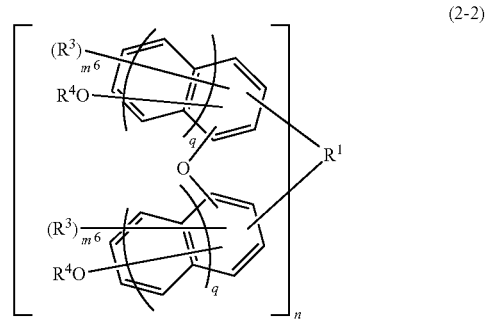

(2-2)

wherein $R^1$ is a 2n-valent group of 1 to 30 carbon atoms; each $R^3$ is independently a halogen atom, a linear, branched, or cyclic alkyl group of 1 to 10 carbon atoms, an aryl group of 6 to 10 carbon atoms, or an alkenyl group of 2 to 10 carbon atoms, and may be the same or different on the same naphthalene ring or benzene ring; each $R^4$ is independently a hydrogen atom or an acid dissociation group; n is an integer of 1 to 4, and when n is an integer of 2 or greater, structural formulae of n repeating units may be the same or different; each $m^6$ is independently an integer of 0 to 5, and each q is independently 0 or 1; provided that in the general formula (2-2), at least one $R^4$ is an acid dissociation group, and $R^1$ is a group comprising an iodine atom.

13. The compound according to claim 10, wherein the compound represented by the above general formula (2) is a compound represented by the following general formula (4):

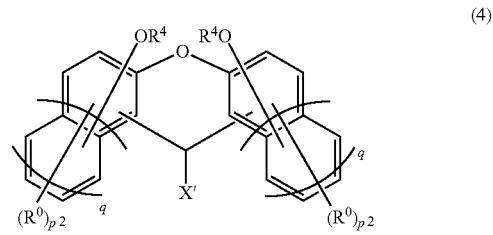

(4)

wherein X' is a halogen atom, or a monovalent group of 1 to 18 carbon atoms; each $R^0$ is independently an alkyl group of 1 to 4 carbon atoms or a halogen atom, and may be the same or different on the same naphthalene ring or benzene ring; $R^4$ is a hydrogen atom or an acid dissociation group; each $p^2$ is independently an integer of 0 to 5; and each q is independently 0 or 1; provided that in the general formula (4), at least one $R^4$ is an acid dissociation group, and X' is a group comprising an iodine atom.

14. A resin obtained by using the compound according to claim 6 as a monomer.

15. The resin according to claim 14 obtained by reacting the compound according to claim 9 with a crosslinking compound.

16. The resin according to claim 15, wherein the crosslinking compound is an aldehyde, a ketone, a carboxylic acid, a carboxylic acid halide, a halogen-containing compound, an amino compound, an imino compound, an isocyanate, or an unsaturated hydrocarbon group-containing compound.

17. A purification method comprising the steps of:
obtaining a solution (A) by dissolving the compound according to claim 9 or the resin according to claim 14 in a solvent; and
extracting impurities in the compound by bringing the obtained solution (A) into contact with an acidic aqueous solution (a first extraction step), wherein
the solvent used in the step of obtaining the solution (A) comprises an organic solvent that does not inadvertently mix with water.

18. The purification method according to claim 17, wherein
the acidic aqueous solution is an aqueous mineral acid solution or an aqueous organic acid solution;
the aqueous mineral acid solution is one or more aqueous mineral acid solutions selected from the group consisting of hydrochloric acid, sulfuric acid, nitric acid, and phosphoric acid; and
the aqueous organic acid solution is one or more aqueous organic acid solutions selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid.

19. The purification method according to claim 17, wherein the organic solvent that does not inadvertently mix with water is one or more organic solvents selected from the group consisting of toluene, 2-heptanone, cyclohexanone, cyclopentanone, methyl isobutyl ketone, propylene glycol monomethyl ether acetate, and ethyl acetate.

20. The purification method according to claim 17, comprising the step of extracting impurities in the compound by further bringing a solution phase comprising the compound into contact with water after the first extraction step (a second extraction step).

* * * * *

UNITED STATES PATENT AND TRADEMARK OFFICE
CERTIFICATE OF CORRECTION

PATENT NO. : 11,256,170 B2
APPLICATION NO. : 15/560059
DATED : February 22, 2022
INVENTOR(S) : Toida et al.

Page 1 of 1

It is certified that error appears in the above-identified patent and that said Letters Patent is hereby corrected as shown below:

In the Specification

At Column 1, Line (4), before the section header "TECHNICAL FIELD," please insert:
-- CROSS-REFERENCE TO RELATED APPLICATIONS
This application is a U.S. national phase application filed under 35 U.S.C. § 371 of International Application PCT/JP2016/056332, filed on March 02, 2016, designating the United States, which claims priority from Japanese Application Number 2015-073497, filed March 31, 2015, which are hereby incorporated herein by reference in their entirety. --.

In the Claims

Column 83, Line (11):
In Claim 5, please delete "R4" and insert -- $R^4$ --, therefor.

Column 87, Line (15):
In Claim 15, please delete "according to claim 9".

Column 87, Line (25):
In Claim 17, please delete "claim 9" and insert -- claim 6 --, therefor.

Column 87, Line (25):
In Claim 17, please delete "or the resin according to claim 14".

Signed and Sealed this
Sixth Day of September, 2022

Katherine Kelly Vidal
*Director of the United States Patent and Trademark Office*